United States Patent
Yi et al.

(10) Patent No.: US 9,812,658 B2
(45) Date of Patent: Nov. 7, 2017

(54) PORPHYRIN BASED SENSITIZER FOR DYE-SENSITIZED SOLAR CELL

(71) Applicant: Ecole Polytechnique Federale de Lausanne (EPFL), Lausanne (CH)

(72) Inventors: Chenyi Yi, Ecublens (CH); Fabrizio Giordano, Lausanne (CH); Shaik Mohammad Zakeeruddin, Bussigny-Lausanne (CH); Michael Graetzel, St-Sulpice (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 0 days.

(21) Appl. No.: 15/101,975

(22) PCT Filed: Dec. 4, 2014

(86) PCT No.: PCT/IB2014/066581
§ 371 (c)(1),
(2) Date: Jun. 6, 2016

(87) PCT Pub. No.: WO2015/087210
PCT Pub. Date: Jun. 18, 2015

(65) Prior Publication Data
US 2016/0308150 A1 Oct. 20, 2016

(30) Foreign Application Priority Data
Dec. 13, 2013 (EP) ..................... 13197269

(51) Int. Cl.
*C07D 487/22* (2006.01)
*H01L 51/00* (2006.01)
*C09B 47/00* (2006.01)
*C07F 3/06* (2006.01)
*H01G 9/20* (2006.01)

(52) U.S. Cl.
CPC ............ *H01L 51/0092* (2013.01); *C07F 3/06* (2013.01); *C09B 47/00* (2013.01); *H01G 9/2031* (2013.01); *H01G 9/2059* (2013.01); *H01G 9/2018* (2013.01); *Y02E 10/542* (2013.01); *Y02E 10/549* (2013.01)

(58) Field of Classification Search
CPC .................................. C07D 487/22
See application file for complete search history.

(56) References Cited

U.S. PATENT DOCUMENTS

2010/0125136 A1 5/2010 Yeh et al.
2013/0090469 A1 4/2013 Yeh et al.

FOREIGN PATENT DOCUMENTS

WO 2007107961 A1 9/2007
WO 2009083901 A1 7/2009

OTHER PUBLICATIONS

Zhang et al. Rational modifications on champion porphyrin dye SM315 using different electron-withdrawing moieties toward high performance dye-sensitized solar cells (Phys. Chem. Chem. Phys., 2014, 16, 24994-25003).*
International Search Report; European Patent Office; International Application No. PCT/IB2014/066581; dated Jun. 18, 2015; 4 pages.
Written Opinion of the International Searching Authority; European Patent Office; International Application No. PCT/IB2014/066581; dated Jun. 18, 2015; 8 pages.
Hsueh-Pei Lu et al.; Design and Characterization of Highly Efficient Porphyrin Sensitizers or Green See-Through Dye-Sensitized Solar Cells; Physical Chemistry Chemical Physics; Nov. 28, 2009; vol. 11 No. 44; 6 pages.
Chou-Pou Hsieh et al.; Synthesis and Characterization of Porphyrin Sensitizers with Various Electron-Donating Substituents for Highly Efficient Dye-Sensitized Solar Cells; Journal of Materials Chemistry; 2010; vol. 20; 8 pages.
Takeru Bessho et al.; Highly Efficient Mesoscopic Dye-Sensitized Solar Cells Based on Donor-Acceptor-Substituted Porphyrins; Angew. Chem. Int.; 2010; vol. 49; 4 pages.
Aswani Yella et al; Porphyrin-Sensitized Solar Cells with Cobalt (II/III)-Based Redox Electrolyte Exceed 12 Percent Efficiency; Science; Nov. 4, 2011; vol. 334; 8 pages.
Seigo Ito et al.; High-Conversion-Efficiency Organic Dye-Sensitized Solar Cells With a Novel Indoline Dye; Chem. Commun.; 2008; 3 pages.

* cited by examiner

*Primary Examiner* — Brian McDowell
(74) *Attorney, Agent, or Firm* — Taft Stettinius & Hollister LLP

(57) ABSTRACT

The present invention relates to compounds of formula (I)

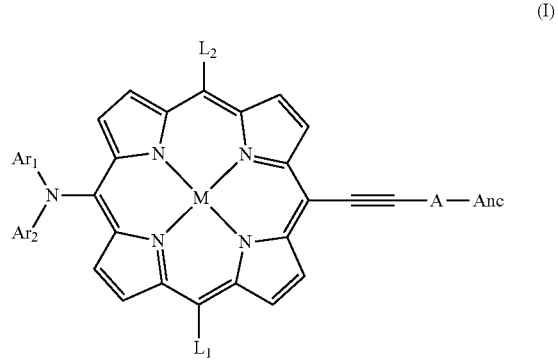

based on a porphyrin core and a π-conjugated linker or acceptor introduced between the porphyrin core and an anchoring group having a high absorption coefficient covering the whole UV-Visible and near-infrared spectral response, and their use as sensitizer or dye and an electrochemical or optoelectronic device including a compound of the invention.

12 Claims, 5 Drawing Sheets

A

B

A

B

PORPHYRIN BASED SENSITIZER FOR DYE-SENSITIZED SOLAR CELL

This application is a U.S. national stage filing of International Application No. PCT/IB2014/066581 filed on Dec. 4, 2014, which claims priority to European Application No. 13197269.7 filed on Dec. 13, 2013, the contents of each application incorporated herein by reference in their entirety.

TECHNICAL FIELD

The present invention relates to porphyrin based compounds to use as sensitizers or zinc porphyrin-based photosensitizing compounds providing efficient charge transfer flow from the donor to the acceptor moiety which anchors the dye to the surface of the oxide scaffold acting as electron acceptor. The present invention further relates to porphyrin photosensitizing dyes covering the whole UV-Visible to near-infrared region spectrum with high absorption coefficient to increase the photoelectric conversion efficiency, to their use in photoelectrochemical, electrochemical or optoelectronic device, in particular dye-sensitized solar cells (DSCs) comprising such zinc porphyrin-based photosensitizer compounds.

PRIOR ART AND THE PROBLEM UNDERLYING THE INVENTION

The worlds increasing demand for energy and global warming alarming us to reduce the use of fossil fuels and find alternate renewable energy sources. In field of solar energy conversion to electricity, the dye sensitized solar cells (DSCs) have attracted considerable attention in recent years due to its low cost and high efficiency. For example, DSCs based on ruthenium sensitizers have reached overall power conversion efficiency (PCE) of over 11% under standard Air Mass 1.5 G illumination.

In recent years many efforts have been devoted to develop organic sensitizers for practical use due to their high molar absorption coefficients, ease of synthesis and structural modifications and to avoid the use of costly metal having limited availability.

Thus, PCE of donor-π-acceptor (D-π-A) organic sensitizers are attractive candidates to be used as sensitizers for DSC, since they reach more than 10% power conversion efficiency (Ito et al., Chem Commun., 2008, 5194).

Porphyrins have large absorption coefficients of their Soret and Q-bands in the visible region. They are also considered as being very attractive sensitizers. Further these phorphyrin sensitizers may be functionalized at the meso and beta positions of the chromophore to tune the spectral properties and energetics of porphyrins.

In the family of porphyrins, introducing donor and acceptor moieties and using zinc porphyrin chromophore as a π-bridge strategy has been produced a new family of efficient sensitizers by creating judicious directional electron flow from the donor to the acceptor moiety which anchors the dye to the surface of the oxide scaffold acting as electron acceptor (US 2010/0125136, US 2013/0090469). But the power conversion efficiency of DSCs comprising such sensitizers are low and remains under 10%.

In the absorption spectrum of porphyrins there is a valley or gap around 500 nm between the Soret and Q-bands. This valley is also described in Lu et al. (Phys. Chem. Chem. Phys., 2009, pp. 10270-10274), wherein the porphyrin dyes comprise an acceptor composed of a π-conjugation bridge and a carboxylic anchoring group. To overcome this valley and to obtain an absorbing broad spectral response, the co-sensitization approach by combining a donor-acceptor zinc porphyrin, with an organic co-sensitizer dye, in conjunction with a cobalt redox electrolyte was used to enhance the device performance (Yella et al., Science, 2011, 334, 629-634).

The present invention addresses the disadvantage of the organic sensitizer, in particular Ruthenium based dyes and porphyrin based dyes spectral response. The present invention also addresses the problem of the decreased light absorption around 500 nm (the "valley") and to broadening the spectral response of said porphyrin dyes by avoiding the co-sensitization approach by two dyes containing complimentary absorption spectra.

The invention pursues to provide a new porphyrin sensitizer or porphyrin dye without using costly metals having limited availability and which does not require further co-sensitizers dye for complementing the light-absorption spectrum of porphyrin based dye. Said porphyrin dyes of the invention have a broad light absorption spectrum and have an extra charge transition band to fill the valley between the Soret and Q-bands. Thus the co-sensitization with a dye having complementary absorption spectrum is not needed to obtain high PCE and to enhance photoelectrochemical devices comprising such a dye. Further the porphyrin dyes are highly efficient, low cost and show good stability in addition to show an extension of light harvesting into the near IR.

The present invention addresses the problems depicted above.

SUMMARY OF THE INVENTION

Surprisingly the present inventors have found that the introduction of an electron-acceptor as π-conjugated linker between the anchoring group and the porphyrin chromophore or core contributes to the extra charge transition band to fill the valley between the Soret and Q-bands. The introduction of an electron acceptor such as quinoxaline based spacer between the porphyrin core and the anchoring group derived from benzoic acid provides new porphyrin sensitizing compounds with a broad absorption covering the whole UV-Visible spectrum to the near-IR (infrared) spectrum.

Surprisingly, it is observed that compared with a reference porphyrin sensitizer without the quinaxoline based electron-acceptor, the compound of the invention also presents a red-shifted spectrum in addition to bridge the absorption gap between the Soret band and Q band and improves the energy conversion efficiency of porphyrin dye-sensitized solar cells comprising such a dye. The co-sensitization with two dyes, of which one is a former porphyrin dye, is not necessary to increase the energy conversion efficiency. The sensitization with one dye of the invention is sufficient to obtain a device with a power conversion efficiency of more than 12%.

In an aspect, the present invention provides a compound of formula I
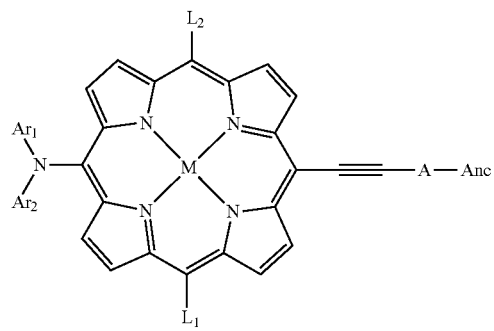
(I)
wherein
M is selected from Co, Cu, Fe, Mg, Mn, Ni, Si or Zn or M is two H (hydrogen) substituting two pyrrole moieties constituting the porphyrin core;
A is an acceptor group selected from a moiety according to any one of the formulae (1) to (36) and (103) to (107)
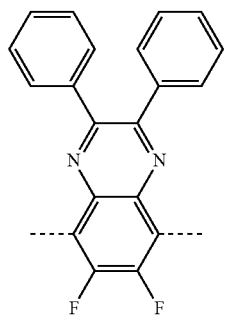
(1)
(2)
(3)
-continued
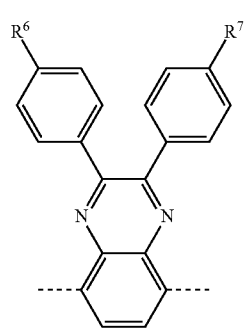
(4)
(5)
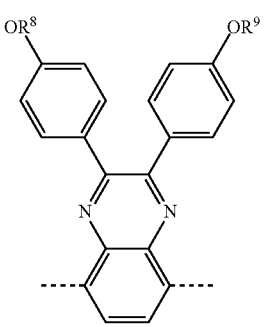
(6)
(7)
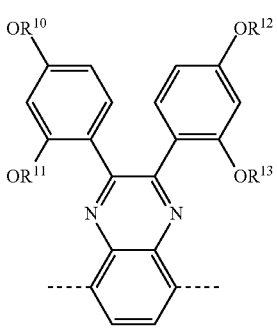
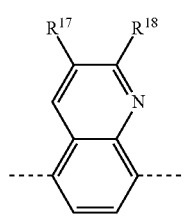
(8)

(9)
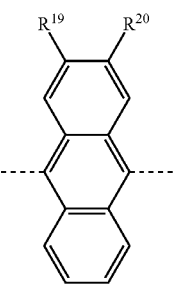
(10)
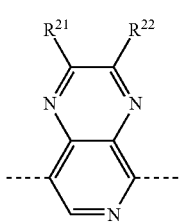
(11)
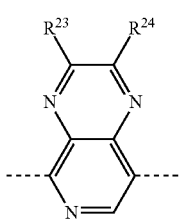
(12)
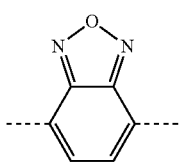
(13)
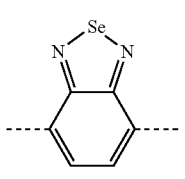
(14)
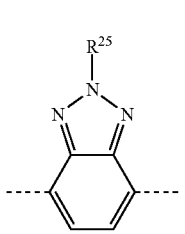
(15)
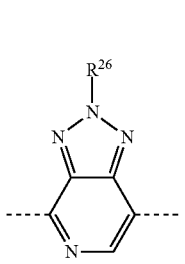
(16)
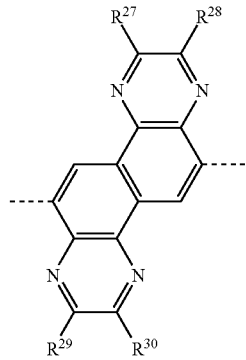
(17)
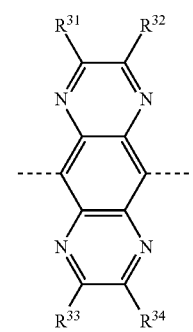
(18)
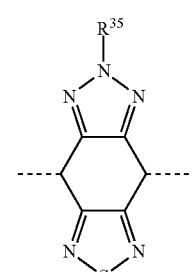
(19)
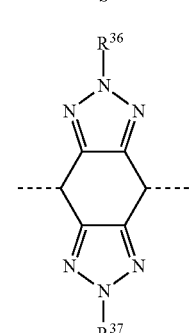
(20)
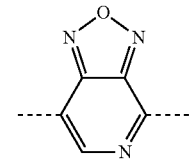
(21)
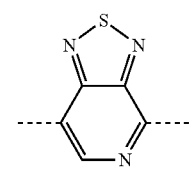

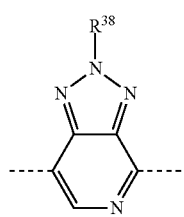
(22)
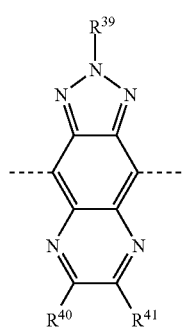
(23)
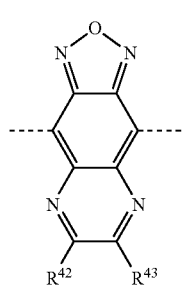
(24)
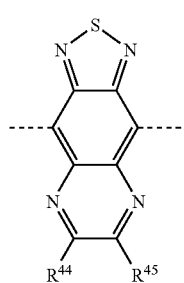
(25)
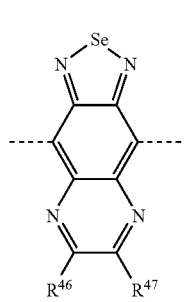
(26)
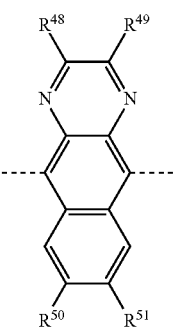
(27)
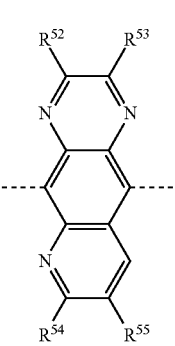
(28)
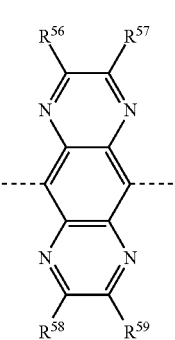
(29)
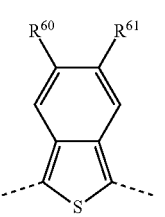
(30)
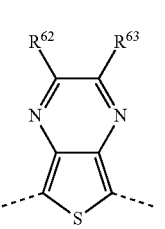
(31)
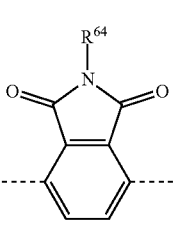
(32)

wherein $R^1$-$R^{68}$ and $R^{137}$-$R^{141}$ are substituents independently selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N;

Anc is an anchoring group selected from C4-C16 aryl or C4-C16 heteroaryl being further substituted, wherein heteroatoms are selected from O, S, or N and wherein further substituents are selected from COOH, =O (keto), C4-C16 cyanoalkenyl carboxylic acid;

$L_1$ and $L_2$ are substituents independently selected from C4-C16 aryl or C4-C16 heteroaryl being further substituted or unsubstituted, wherein heteroatoms are selected from O, S, or N and wherein the further substituents are selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N;

$Ar_1$ and $Ar_2$ are donor substituents being selected from C4-C16 aryl, C8-C32-diaryl, C4-C16 heteroaryl being further substituted or unsubstituted, wherein heteroatoms are selected from O, S, or N and wherein the further substituents are selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N.

In a further aspect, the invention provides the use of said compound of formula (I) as a dye or a sensitizing compound in an electrochemical or optoelectronic device.

In another aspect, the present invention provides an electrochemical, preferably photoelectrochemical, or optoelectronic device comprising a dye being said compound of formula (I).

Further aspects and preferred embodiments of the invention are defined herein below and in the appended claims. Further features and advantages of the invention will become apparent to the skilled person from the description of the preferred embodiments given below.

DETAILED DESCRIPTION OF THE PREFERRED EMBODIMENTS

Figure 1:
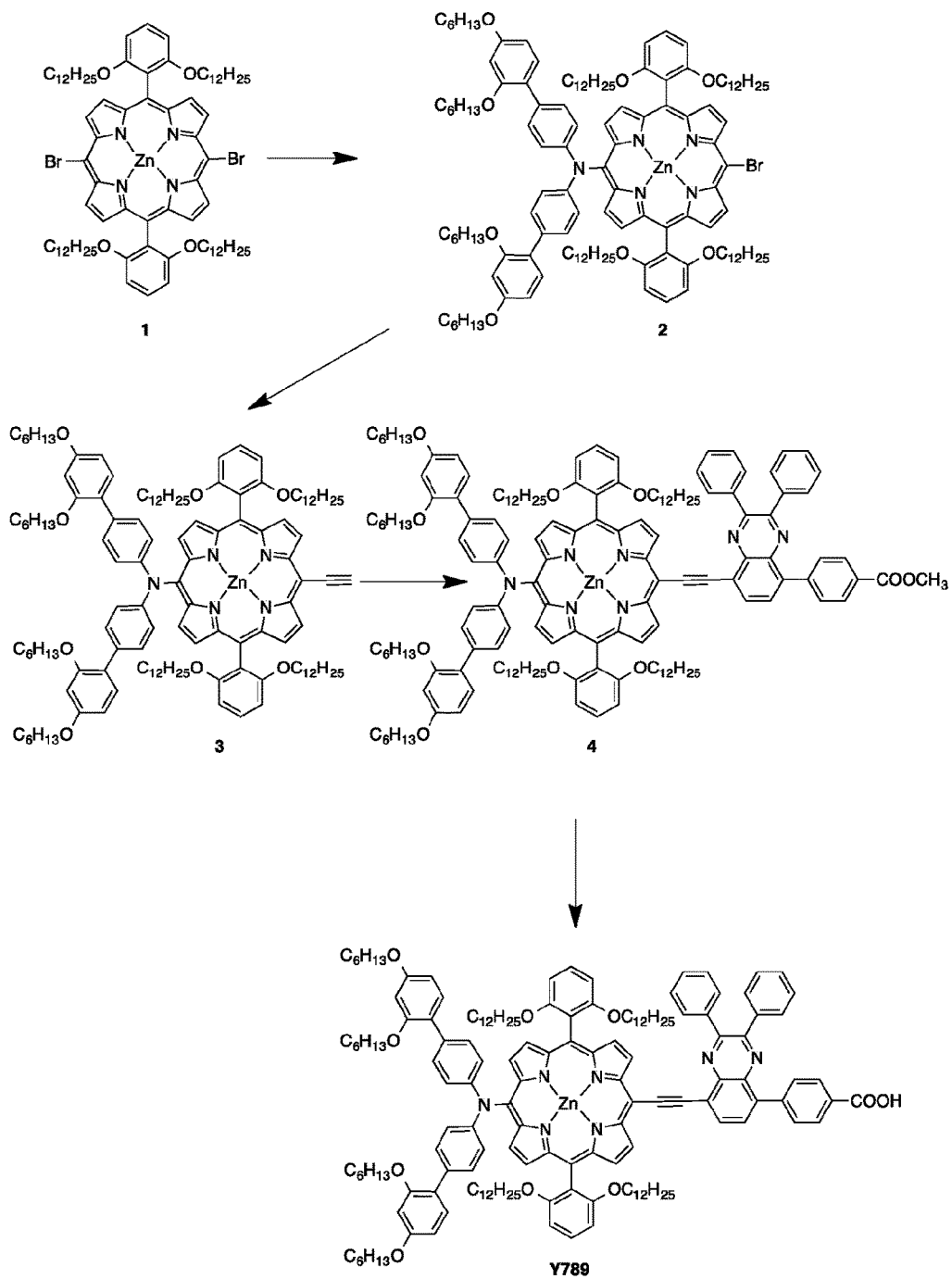
FIG. 1 shows the scheme of synthesis of a compound of the invention of formula (89) or dye Y789.

The present invention concerns compounds based on porphyrin core absorbing on the whole spectrum of UV-Visible and near-IR light spectrum without the requirement of the co-sensitization, their use as sensitizing compound or dye in an electrochemical or optoelectronic device and an electrochemical or optoelectronic devices comprising a compound of the invention.

In particular, the compound of the invention is a compound of formula (I)

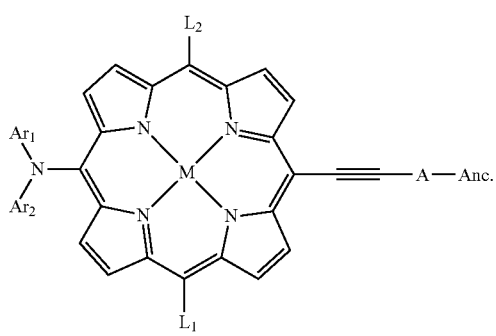

(I)

Without to be bound by the theory, the porphyrin core is tuned to provide the better expected power conversion efficiency (PCE) as sensitizers for electrochemical, photoelectrochemical or optoelectronic device, in particular for DSCs by the introduction of an electron-acceptor (A) as π-conjugated linker between the anchoring group (Anc) and the porphyrin chromophore. Said porphyrin chromophore is further substituted on the meso-10, 20 positions of said porphyrin core by $L_1$ and $L_2$ being a C4-C12 aryl or a C4-C12 heteroaryl, wherein the heteroatom is S, said aryl or heteroaryl being further substituted by alkoxy chain in order to protect the dye from the aggregation. The stereo hindrance between the molecules thus increasing and the π-π interaction of the porphyrin ring itself being reduced, the molecular solubility is enhanced and the aggregation of the molecules is prevented. The porphyrin core is substituted with a donor group, wherein the amino group is further substituted by aromatic group, donor substituents $Ar_1$ and $Ar_2$.

M is a divalent metal, which may be present or absent, and if present M is selected from Co, Cu, Fe, Mg, Mn, Ni, Si or Zn. Preferably M is selected from Co, Cu, or Zn. Most preferably M is Zn. If M is absent, M is replaced by two H (hydrogen) substituting two pyrrole moieties constituting the porphyrin core.

A is an acceptor group selected from a moiety according to any one of the formulae (1) to (36) and (103) to (107)

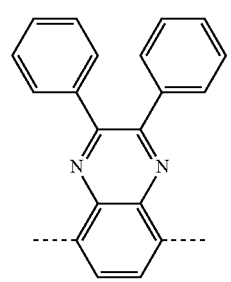

(1)

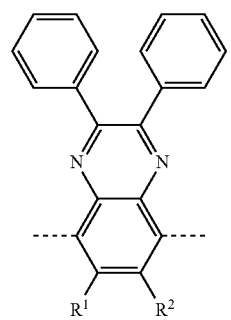

(2)

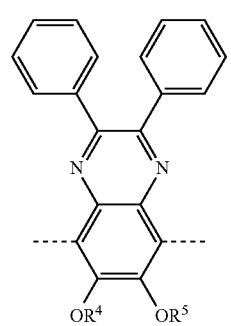

(3)

(4)
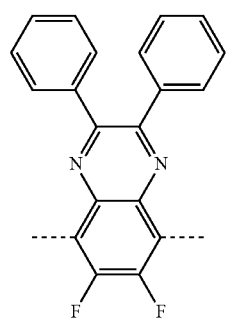
(5)
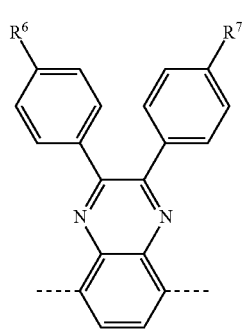
(6)
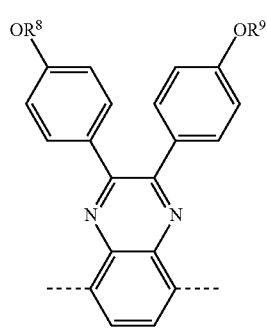
(7)
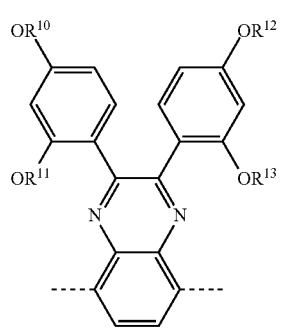
(8)
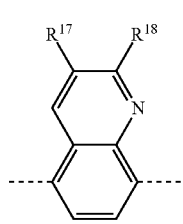
(9)
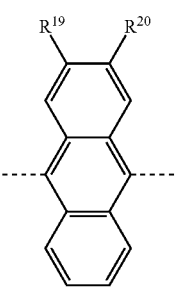
(10)
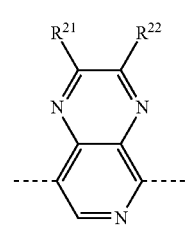
(11)
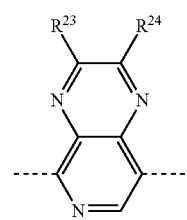
(12)
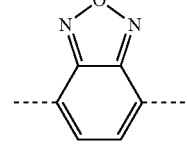
(13)
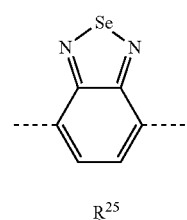
(14)
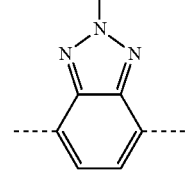
(15)

-continued
(16)
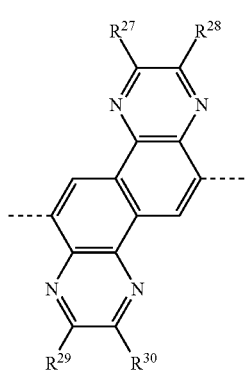
(17)
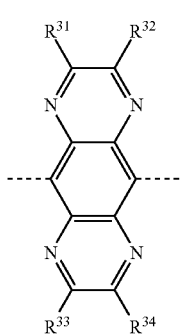
(18)
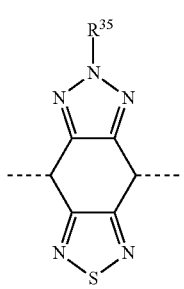
(19)
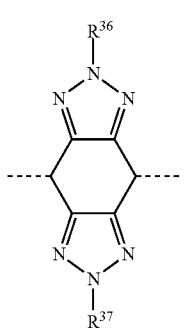
(20)
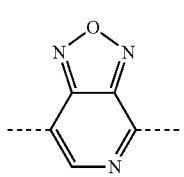
(21)
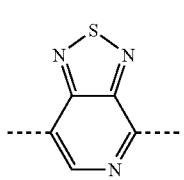
-continued
(22)
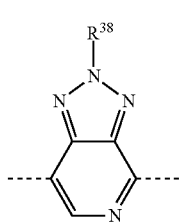
(23)
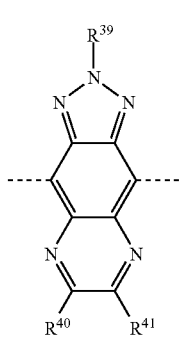
(24)
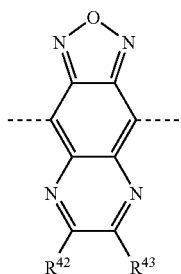
(25)
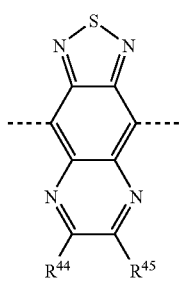
(26)
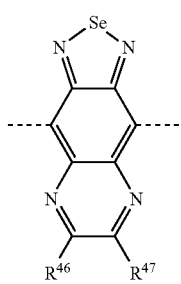

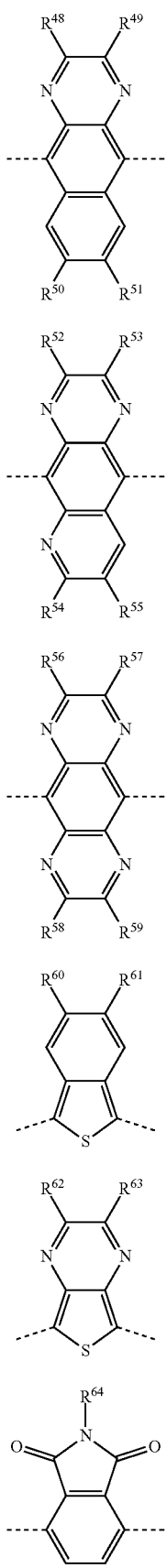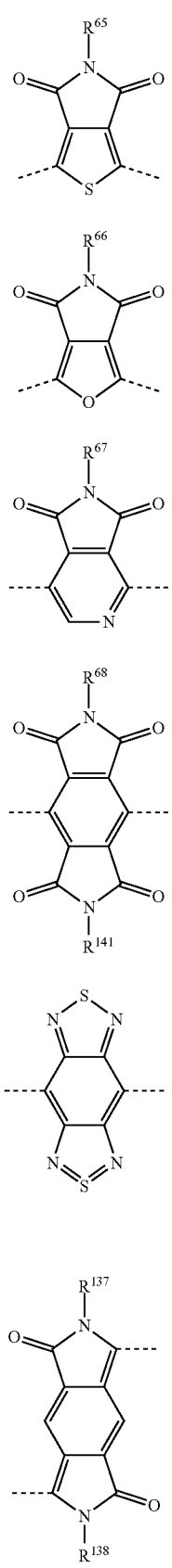

-continued

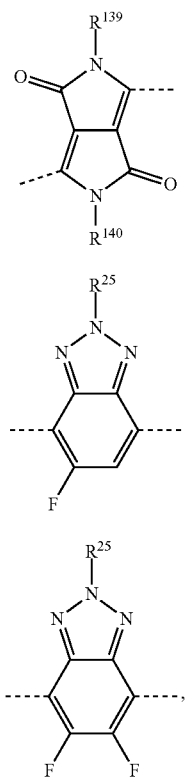

(105)

(106)

(107)

wherein $R^1$-$R^{68}$ and $R^{137}$-$R^{141}$ are substituents independently selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N. If alkyl, alkoxy, thioalkyl, alkoxyalkyl, arylalkyl and heteroaryl groups comprise 3 or more carbons, they may be linear, branched or cyclic. Preferably alkyl, alkoxy, thioalkyl, alkoxyalkyl, arylalkyl and heteroaryl are selected from hydrocarbon containing from 1 to 16 carbons, 1 to 12 carbons or 1 to 8 carbons. Substituents from $R^1$-$R^{68}$ and $R^{137}$-$R^{141}$ substituting the same moiety of same formula may be identical to the other substituent substituting the same moiety of same formula or different. For example, $R^1$ and $R^2$ substituting the moiety of formula (2) may be identical or different.

In a further embodiment, A is an acceptor group selected from a moiety according to any one of the formulae (1) to (36) and (103) to (105)

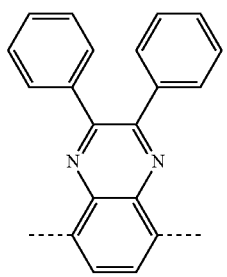

(1)

-continued

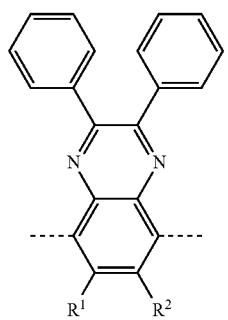

(2)

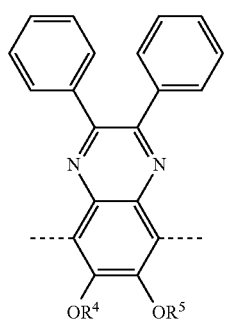

(3)

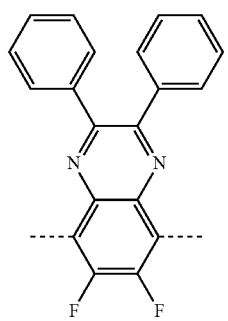

(4)

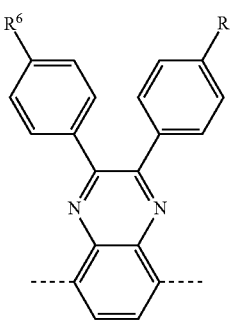

(5)

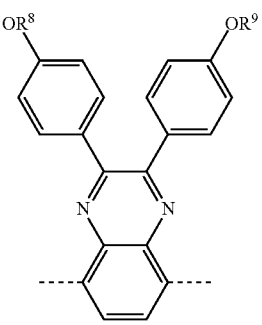

(6)

-continued
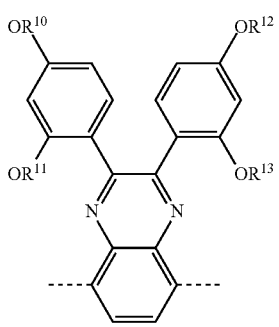
(7)
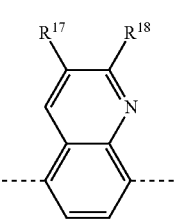
(8)
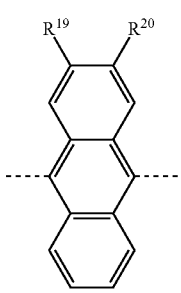
(9)
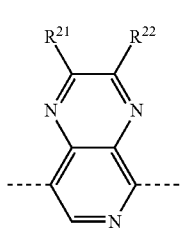
(10)
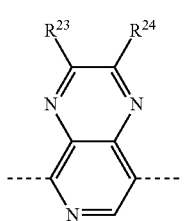
(11)
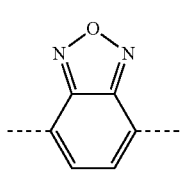
(12)
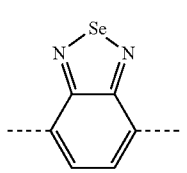
(13)
-continued
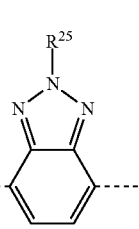
(14)
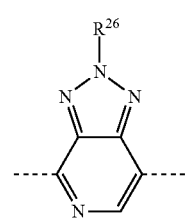
(15)
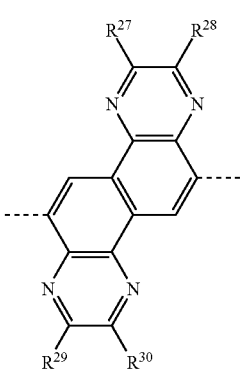
(16)
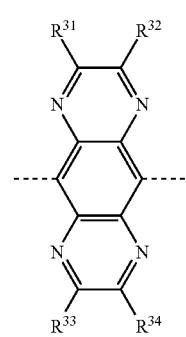
(17)
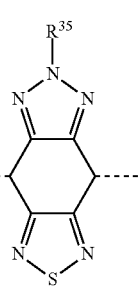
(18)

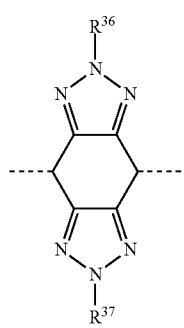
(19)
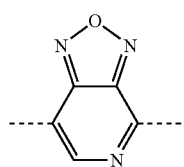
(20)
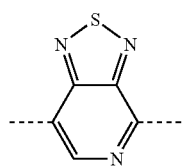
(21)
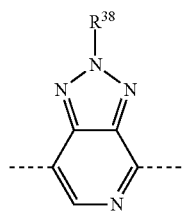
(22)
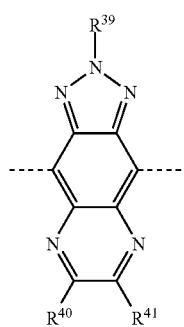
(23)
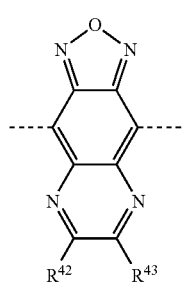
(24)
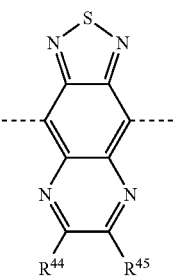
(25)
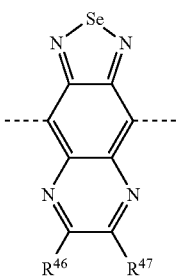
(26)
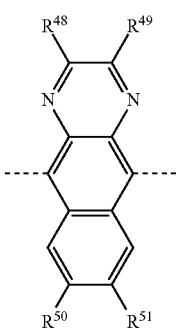
(27)
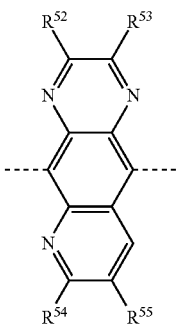
(28)
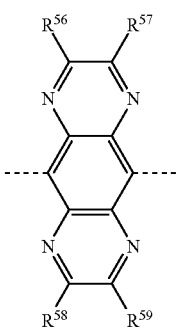
(29)

(30) 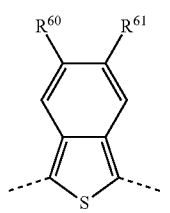

(31) 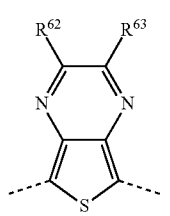

(32) 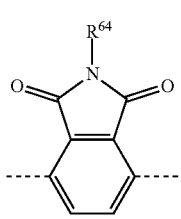

(33) 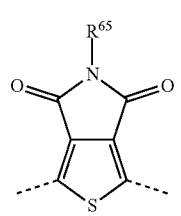

(34) 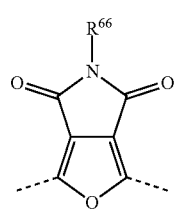

(35) 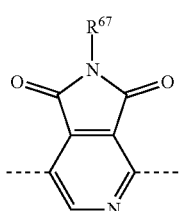

(36) 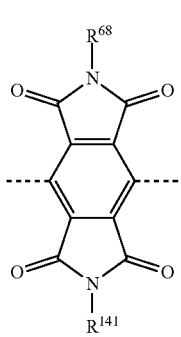

(103) 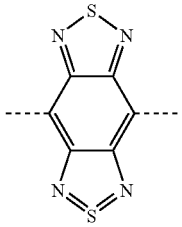

(104) 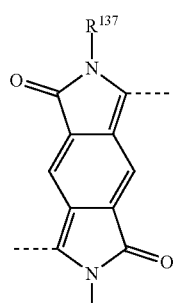

(105) 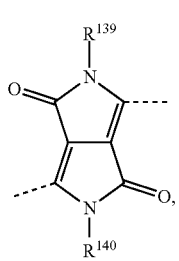

wherein $R^1$-$R^{68}$ and $R^{137}$-$R^{141}$ are substituents independently selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N. If alkyl, alkoxy, thioalkyl, alkoxyalkyl, arylalkyl and heteroaryl groups comprise 3 or more carbons, they may be linear, branched or cyclic. Preferably alkyl, alkoxy, thioalkyl, alkoxyalkyl, arylalkyl and heteroaryl are selected from hydrocarbon containing from 1 to 16 carbons, 1 to 12 carbons or 1 to 8 carbons. Substituents from $R^1$-$R^{68}$ and $R^{137}$-$R^{141}$ substituting the same moiety of same formula may be identical to the other substituent substituting the same moiety of same formula or different. For example, $R^1$ and $R^2$ substituting the moiety of formula (2) may be identical or different.

In a further embodiment of the compound of the invention, the acceptor A is selected from a moiety according to any one of the formulae (1)-(12), (14), (15), (25), (27), (30), and (31). Further A is selected form a moiety according to any one of the formulae (1) to (11), (16), (17) and (27) to (29). Preferably A is selected from a moiety according to any one of the formulae (1) to (11), most preferably from a moiety according to any one of the formulae (1) and (2).

Anc is an anchoring group selected from C4-C16 aryl or C4-C16 heteroaryl being further substituted, wherein heteroatoms are selected from O, S, or N and wherein further substituents are selected from COOH, =O (keto), C4-C16 cyanoalkenyl carboxylic acid.

The anchoring moiety of the anchoring group Anc in the compound of formula (I), preferably being —COOH may be replaced by an anchoring moiety being independently selected from —COOH, PO$_3$H$_2$, —PO$_4$H$_2$, —P(R$_8$)O$_2$H, —SO$_3$H$_2$, —SO$_4$H$_2$, —CONHOH$^-$, 1,2-hydroxybenzene, 1-hydroxy-2-carboxybenzene, acetylacetonate, deprotonated forms of the aforementioned, organic and/or inorganic salts of said deprotonated forms, and chelating groups with π-conducting character. R$_8$ may be a hydrocarbon comprising from 1 to 50 carbons and 0-25 heteroatoms selected from O, N, or S, said hydrocarbon being covalently bound to the P atom of said phosphinic acid group by a carbon atom. R$_8$ may a a substituted or unsubstituted, linear, branched or cyclic C1-C20 alkyl, C2-C20 alkenyl, C2-C20 alkynyl, and C4-C20 aryl.

According to the present invention, the aryl or the heteroaryl moiety may be substituted by abovementioned substituents on the meta-, ortho- or para-position of the aryl or heteroaryl.

In an embodiment, Anc is selected from a moiety according to any one of formulae (37) to (53)

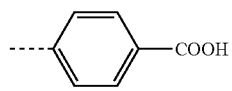
(37)

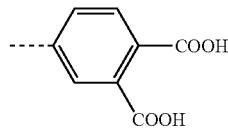
(38)

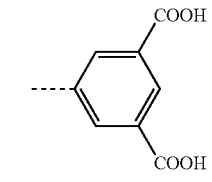
(39)

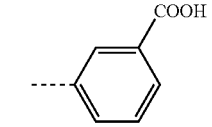
(40)

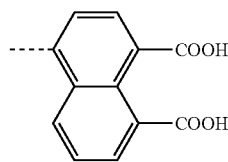
(41)

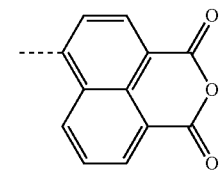
(42)

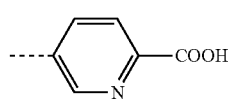
(43)

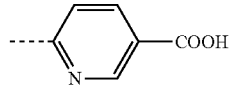
(44)

-continued

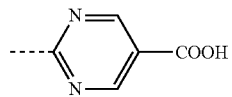
(45)

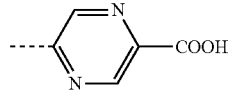
(46)

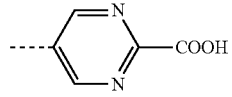
(47)

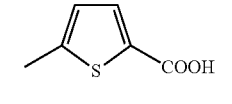
(48)

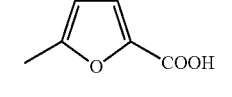
(49)

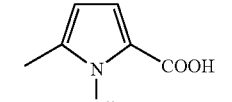
(50)

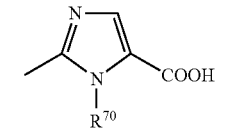
(51)

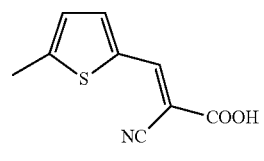
(52)

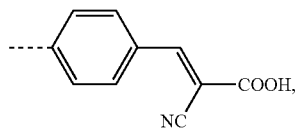
(53)

wherein R$^{69}$ and R$^{70}$ are substituents independently selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N. If alkyl, alkoxy, thioalkyl, alkoxyalkyl, arylalkyl and heteroaryl groups comprise 3 or more carbons, they may be linear, branched or cyclic. Preferably alkyl, alkoxy, thioalkyl, alkoxyalkyl, arylalkyl and heteroaryl are selected from hydrocarbon containing from 1 to 16 carbons, 1 to 12 carbons or 1 to 8 carbons.

In a further embodiment, Anc in the compound of formula (I) is selected from a moiety according to any one of the formulae (37) to (47) or any one of the formulae (37) to (40).

The connection of the compound of the invention onto the semiconductor surface is effected by way of an anchoring group of the compound of the invention. Said connection can be by way of electrostatic interaction and/or of covalent connection and/or coordinate covalent, which is stable for at least 10 hours, preferably at least 10 weeks, mote preferably at least 10 months and ideally up to a more that 1-3 years.

The anchoring group is suitable to anchor said compound of formula (I) onto the surface of a semiconductor. In particular, the compound having the core structure is preferably in any way adsorbed or attached on a surface of said semiconductor, in particular by way of said anchoring group.

$L_1$ and $L_2$ are substituents independently selected from C4-C16 aryl or C4-C16 heteroaryl being further substituted or unsubstituted, wherein heteroatoms are selected from O, S, or N and wherein the further substituents are selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N.

In an embodiment, $L_1$ and $L_2$ are independently selected from a moiety according to any one of formulae (54) to (65)

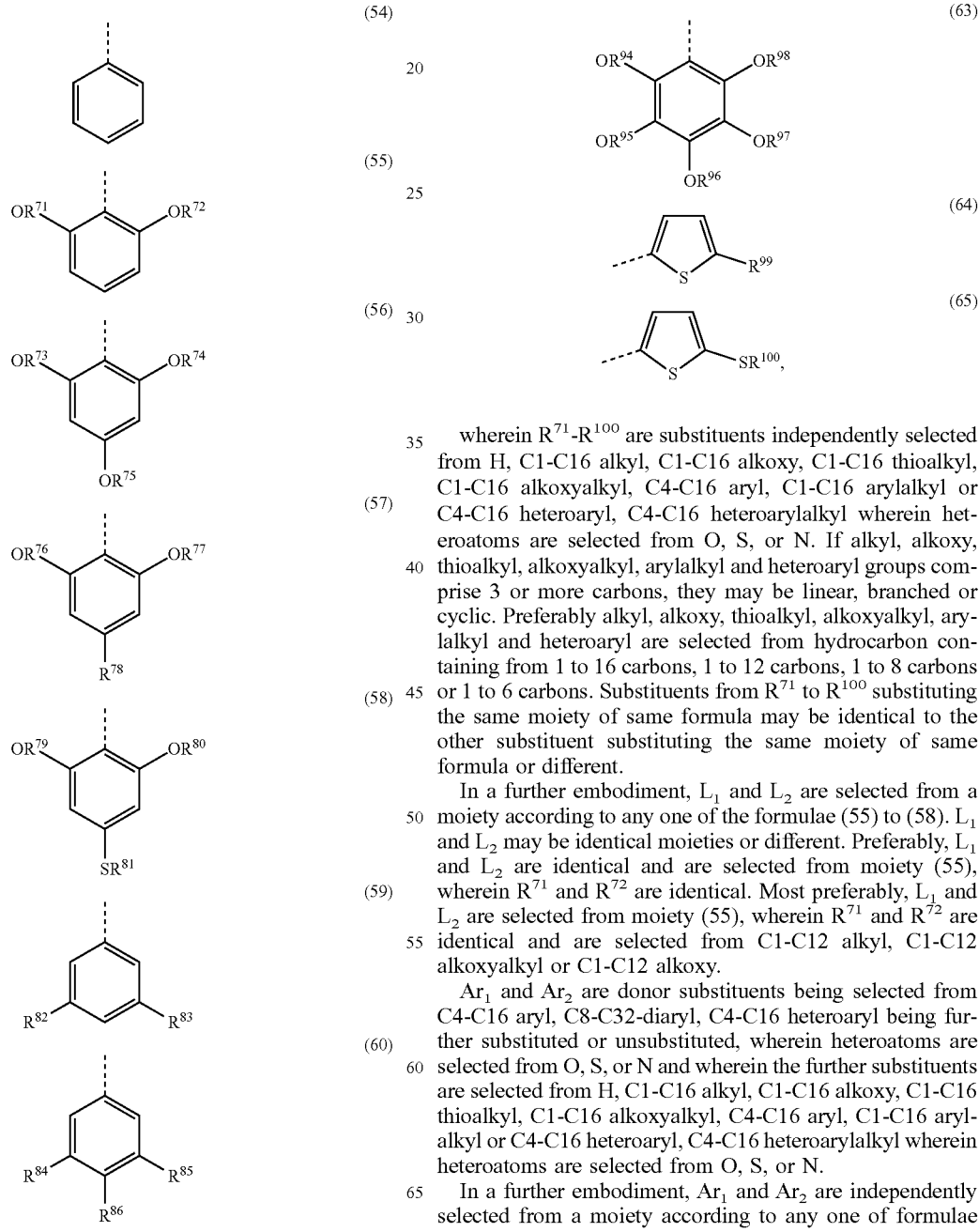

wherein $R^{71}$-$R^{100}$ are substituents independently selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N. If alkyl, alkoxy, thioalkyl, alkoxyalkyl, arylalkyl and heteroaryl groups comprise 3 or more carbons, they may be linear, branched or cyclic. Preferably alkyl, alkoxy, thioalkyl, alkoxyalkyl, arylalkyl and heteroaryl are selected from hydrocarbon containing from 1 to 16 carbons, 1 to 12 carbons, 1 to 8 carbons or 1 to 6 carbons. Substituents from $R^{71}$ to $R^{100}$ substituting the same moiety of same formula may be identical to the other substituent substituting the same moiety of same formula or different.

In a further embodiment, $L_1$ and $L_2$ are selected from a moiety according to any one of the formulae (55) to (58). $L_1$ and $L_2$ may be identical moieties or different. Preferably, $L_1$ and $L_2$ are identical and are selected from moiety (55), wherein $R^{71}$ and $R^{72}$ are identical. Most preferably, $L_1$ and $L_2$ are selected from moiety (55), wherein $R^{71}$ and $R^{72}$ are identical and are selected from C1-C12 alkyl, C1-C12 alkoxyalkyl or C1-C12 alkoxy.

$Ar_1$ and $Ar_2$ are donor substituents being selected from C4-C16 aryl, C8-C32-diaryl, C4-C16 heteroaryl being further substituted or unsubstituted, wherein heteroatoms are selected from O, S, or N and wherein the further substituents are selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N.

In a further embodiment, $Ar_1$ and $Ar_2$ are independently selected from a moiety according to any one of formulae (66) to (88)

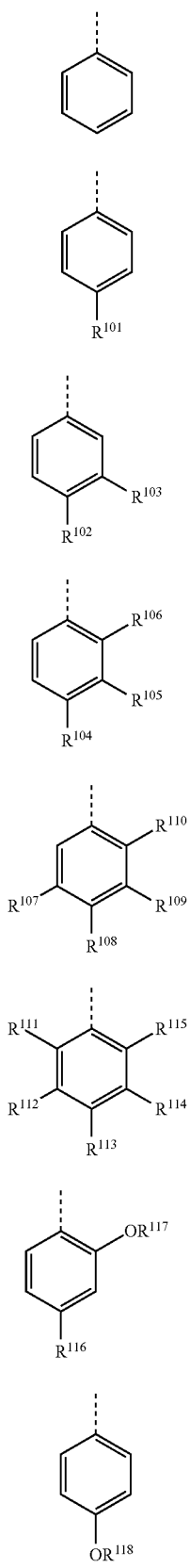

(79) 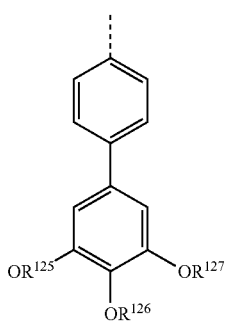

(80) 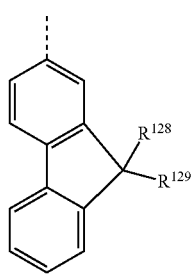

(81) 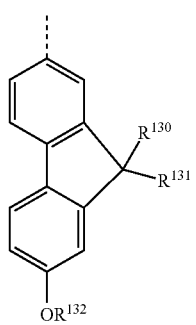

(82) 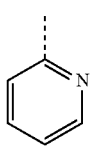

(83) 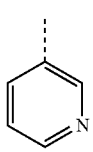

(84) 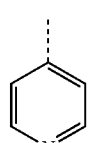

(85) 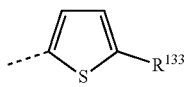

(86) 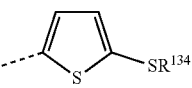

(87) 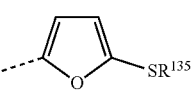

(88) 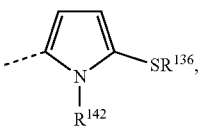

wherein $R^{101}$-$R^{136}$ and $R^{142}$ are substituents independently selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N. If alkyl, alkoxy, thioalkyl, alkoxyalkyl, arylalkyl and heteroaryl groups comprise 3 or more carbons, they may be linear, branched or cyclic. Preferably alkyl, alkoxy, thioalkyl, alkoxyalkyl, arylalkyl and heteroaryl are selected from hydrocarbon containing from 1 to 16 carbons, 1 to 12 carbons, 1 to 8 carbons or 1 to 6 carbons. Substituents from $R^{101}$ to $R^{136}$ and $R^{142}$ substituting the same moiety of same formula may be identical to the other substituent substituting the same moiety of same formula or different.

In a further embodiment, $Ar_1$ and $Ar_2$ are selected from a moiety according to any one of the formulae (67), (75) to (81). $Ar_1$ and $Ar_2$ may be identical moieties or different. Preferably, $Ar_1$ and $Ar_2$ are identical and are selected from moiety (77), wherein $R^{121}$ and $R^{122}$ are identical. Most preferably $Ar_1$ and $Ar_2$ are selected from moiety (77), wherein $R^{121}$ and $R^{122}$ are identical and are selected from C1-C6 alkyl, C1-C6 alkoxyalkyl or C1-C6 alkoxy.

In a further embodiment of the compound of formula (I), $L^1$ and $L^2$ are identical moieties and $Ar^1$ and $Ar^2$ are identical moieties. Accordingly a symmetrical configuration with the porphyrin core is formed.

In the moieties of formula (1) to (88), the connection of any moiety to the basic structure porphyrin core or to a preceding moiety is illustrated by way of a dashed line representing the bond indicating the connection of the moiety to either the porphyrin core and to the following moiety, or to the preceding moiety and the following moiety.

According to an embodiment, the compound of formula (I) is selected from one compound according to any one of formulae (89) to (102):

(89)
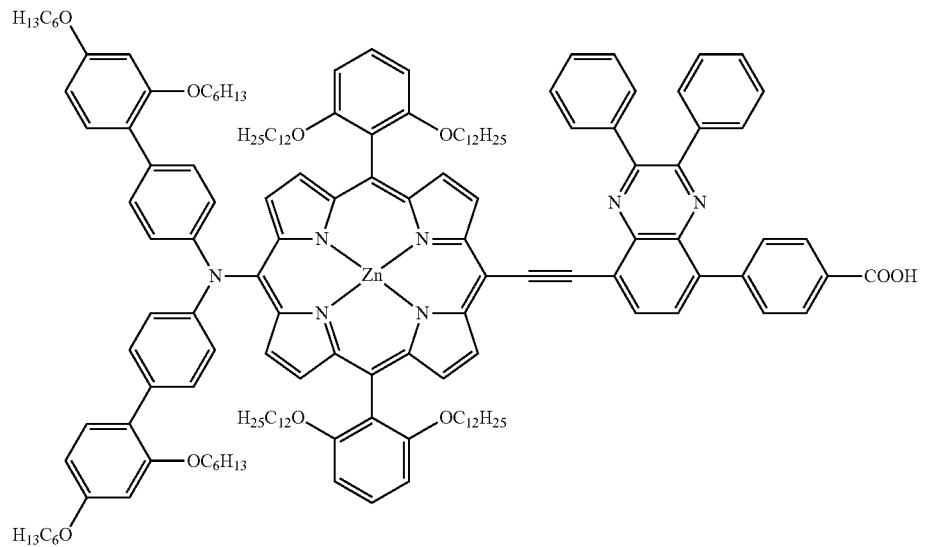
(90)
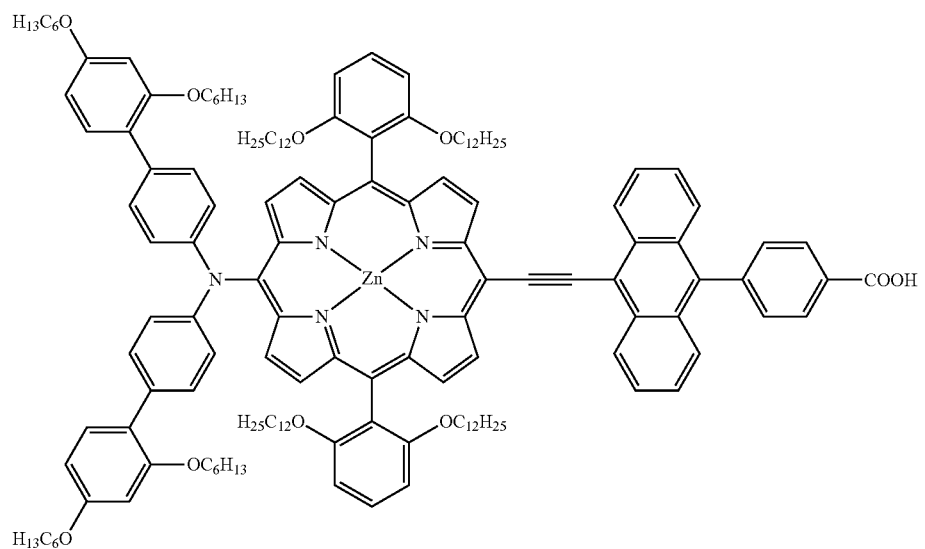
(91)
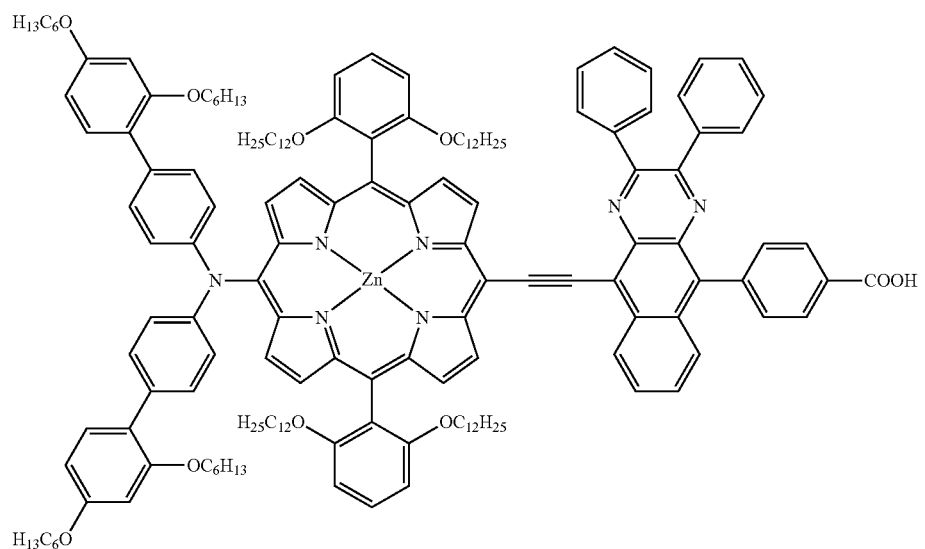

-continued
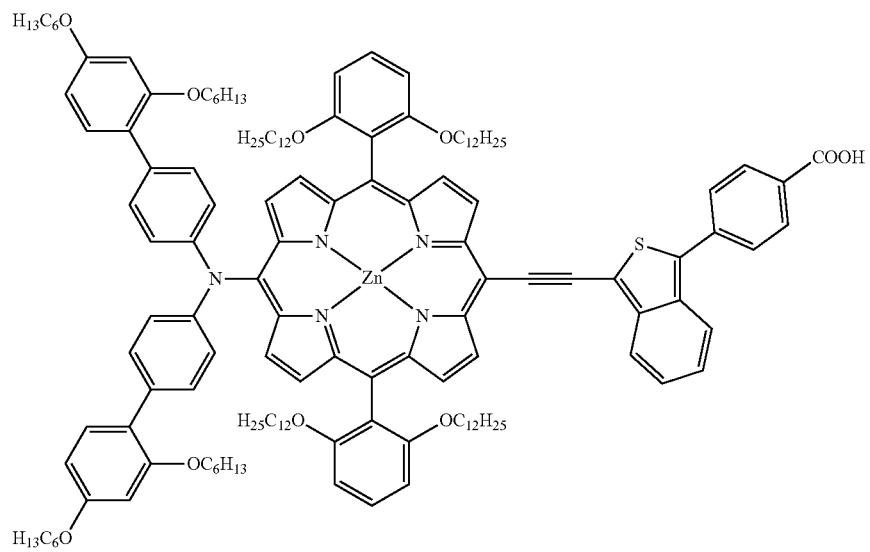
(92)
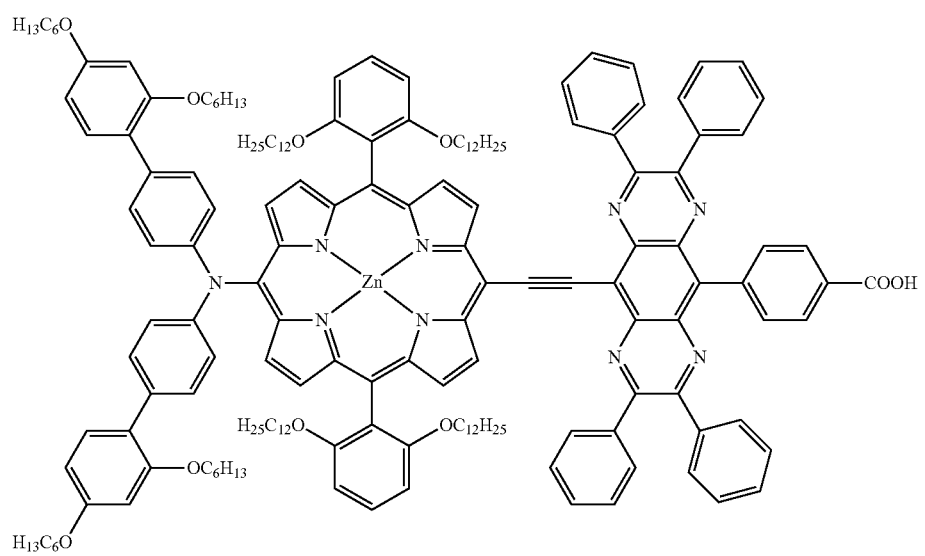
(93)
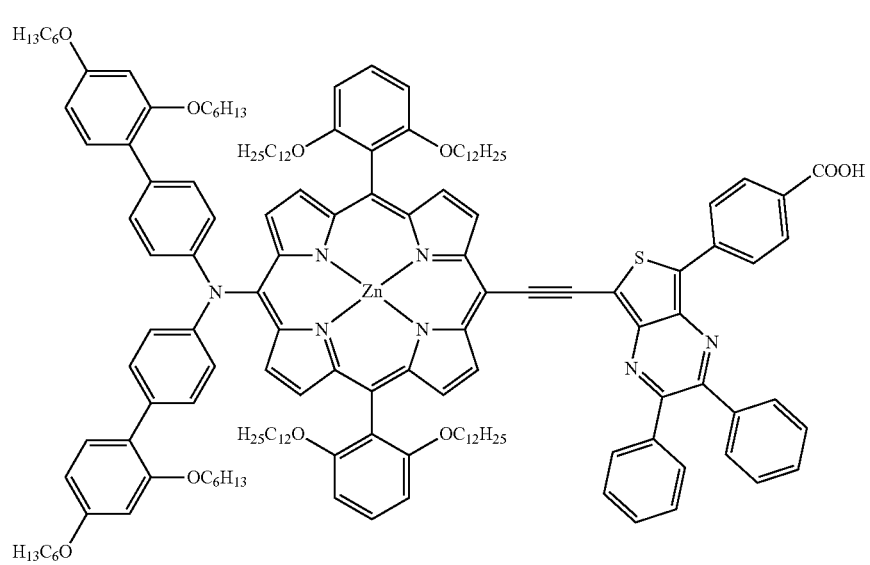
(94)

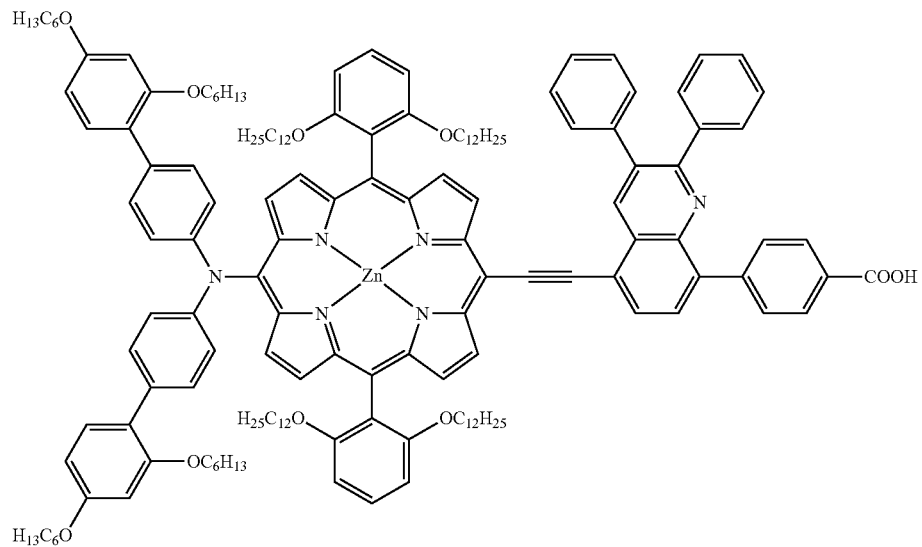
(95)
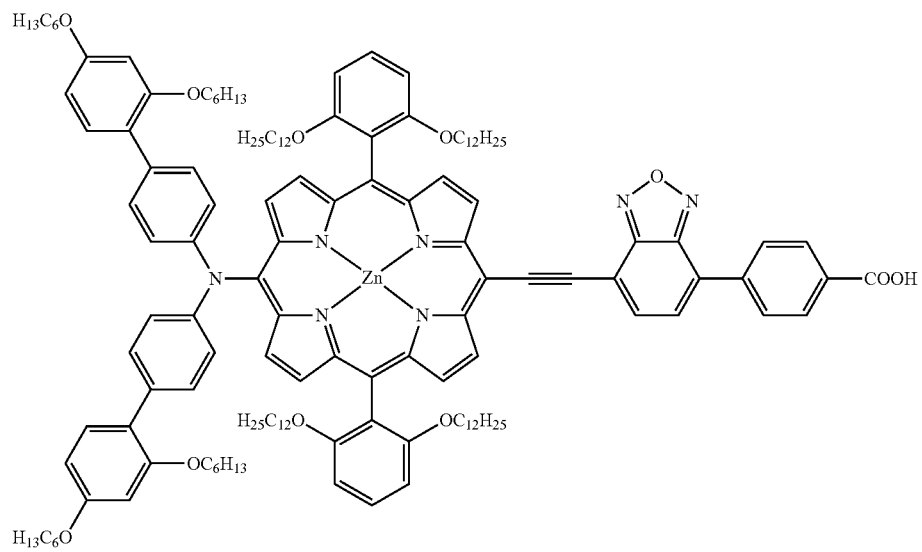
(96)
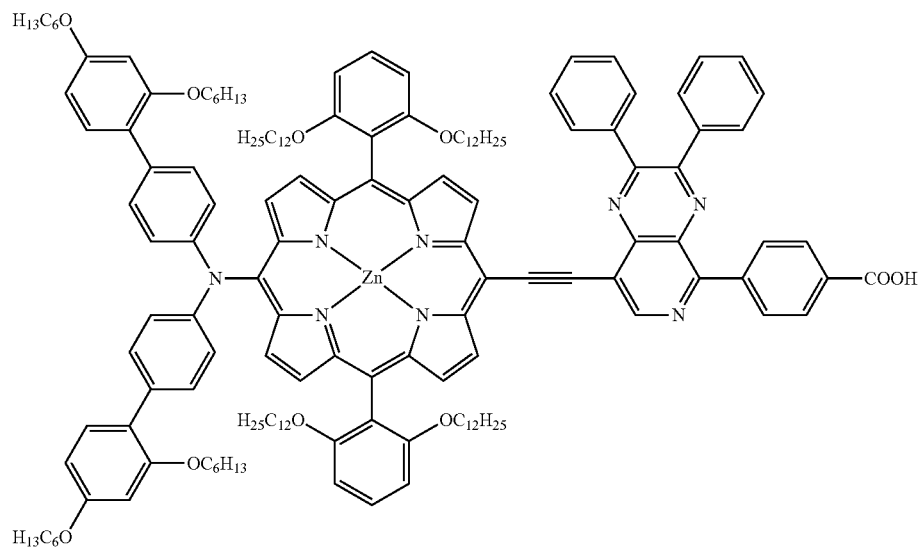
(97)

(98)
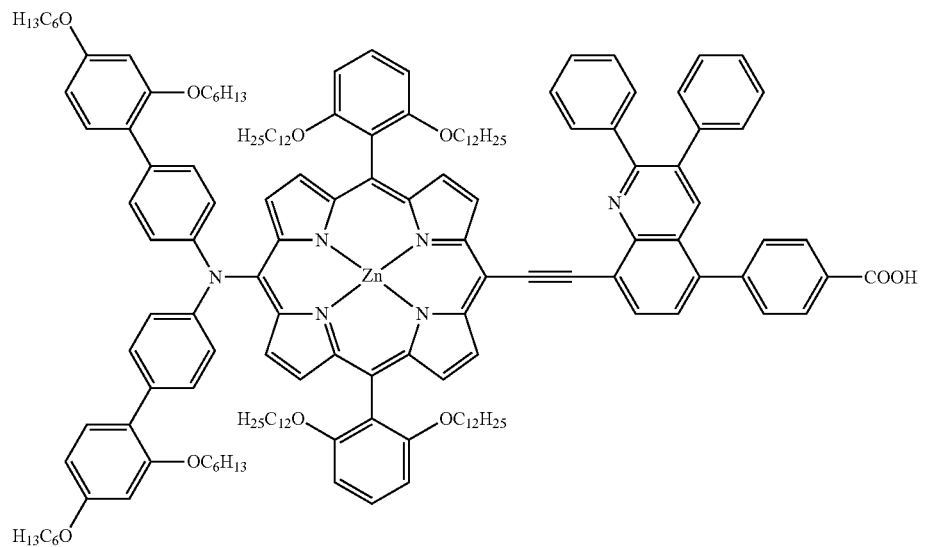
(99)
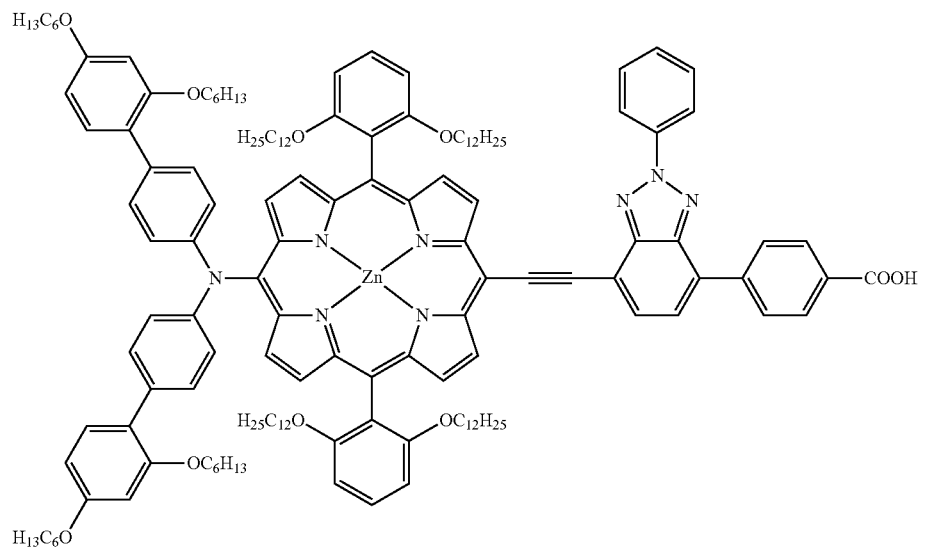
(100)
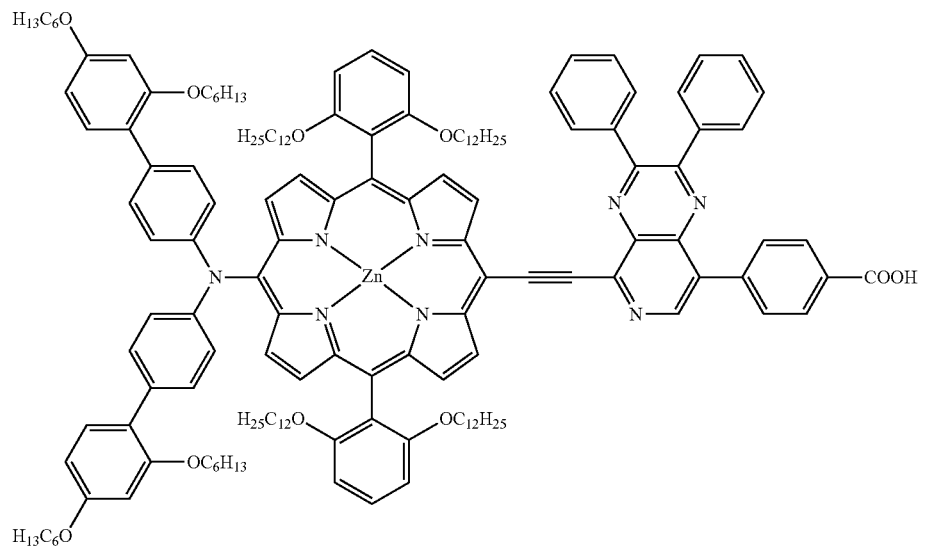

-continued

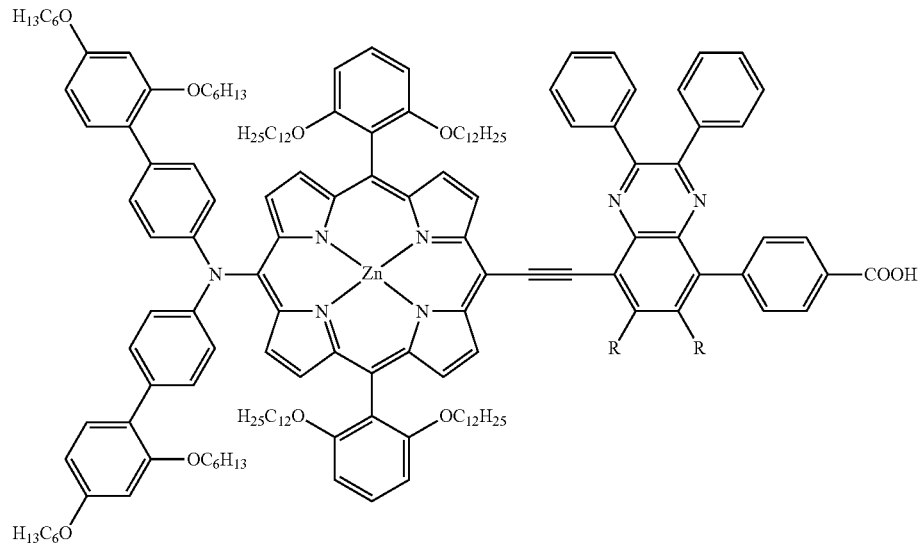

(101)

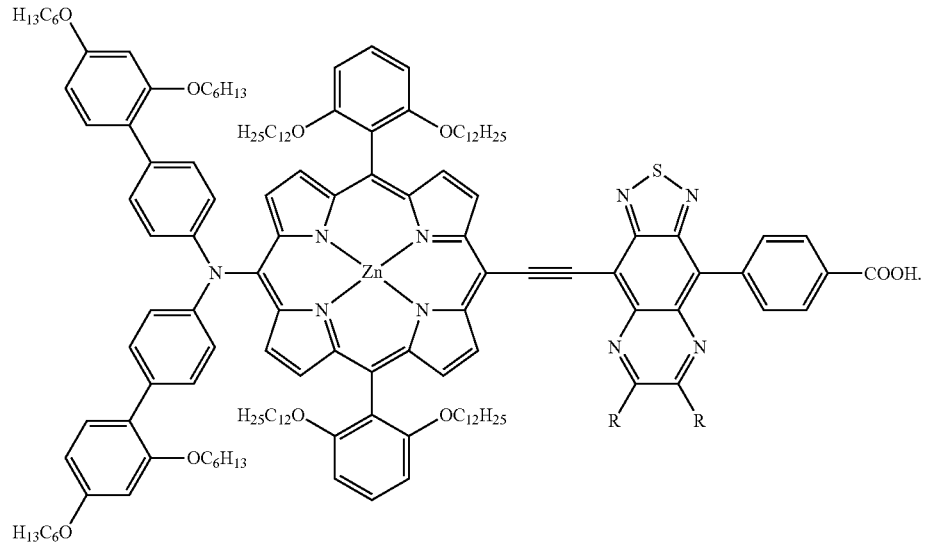

(102)

The invention also provides a use of a compound of formula (I) as a dye or a sensitizing compound in an electrochemical or optoelectronic device.

The meaning of the terms "dye", "sensitizer", "sensitizing dye or compound", "photosensitizer", "dye sensitizer" may partially or totally overlap with each other.

The invention further provides, in one aspect, an electrochemical or optoelectronic device comprising a dye being a compound of formula (I) of the invention.

Figure 7:
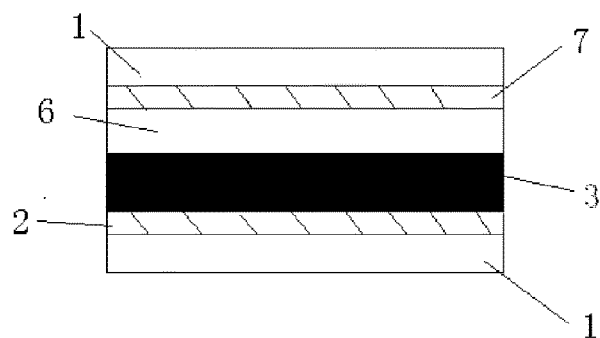
FIG. 7 is a schematic representation of a DSC with a dye according to the present invention.
Figure 8:
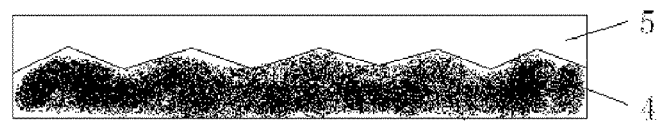
FIG. 8 is a schematic representation of the light adsorption layer 3 shown in FIG. 7, comprising a semiconductor nanoparticle layer 4 and a dye layer 5.

For the purpose of illustration, an exemplary, non-limiting embodiment of a DSC according to the invention is shown in FIGS. 7 and 8. The device comprises a light absorption layer 3 comprising a semiconductor material 4 and, absorbed thereto, a layer 5 comprising a dye according to invention or a dye comprising the compound of the invention.

According to an embodiment, the semiconductor material 4 comprises a porous structure. The porous structure is illustrated by the zigzag line in FIG. 8.

In another embodiment, the device of the invention comprises a semiconductor surface 4 on which the compound of the invention is adsorbed.

According to an embodiment, the device of the invention is selected from an electrochemical device, a photo-electrochemical device, an optoelectronic device, a light emitting device, an electrochromic or photo-electrochromic device, an electrochemical sensor, an electrochemical display or a dye sensitized solar cell.

According to a preferred embodiment, the electrochemical device is a photoelectrical conversion device selected from a solar cell, a dye-sensitized solar cell (DSC), a regenerative dye-sensitized solar cell, a photovoltaic device or a photovoltaic cell. The device of the invention is the most preferably a dye-sensitized solar cell (DSC). In said device, the semiconductor is sensitized by the compound of the invention of formula (I), which may be connected onto the semiconductor surface by way of its anchoring group Anc.

In a further aspect, the present invention provides a method of preparing an electrochemical or optoelectronic device, preferably a DSC, providing a first (electrode 2) and a second electrode (electrode 7), wherein the first electrode is the anode covered by a mesoporous oxide film of $TiO_2$, providing a compound of formula (I) as sensitizer to said mesoporous oxide film of TiO$_2$ and providing an intermediate layer (charge transport layer 6) comprising an electrolyte and a redox couple, or a hole transporting material for solid state devices.

According to a further embodiment, the semiconductor material (layer 4) comprises a porous structure. The device of the invention further comprises at least one substrate 1, an electrode 2 and a counter electrode 7, and a charge transport layer 6, said charge transport layer being provided between said counter electrode and said dye layer 5.

The substrate layer 1 is preferably a transparent substrate layer selected from glass or plastic. Although there are two, a top and a bottom substrate layer 1 as shown in FIG. 7, devices with only one, a top or a bottom transparent substrate layer are also encompassed. Generally, the substrate is then on the side of the counter electrode 7. Exemplary plastic substrates are polyethylene terephthalate, polyethylene naphthalate (PEN), polycarbonate, polypropylene, polyimide, 3-acetyl cellulose, and polyethersulfone (PES).

The conductive layer may be provided by of one of Indium tin oxide (ITO), tin oxide fluoride (FTO), ZnO—Ga$_2$O$_3$, ZnO—Al$_2$O$_3$, tin-oxide, antimony tin oxide (ATO) and zinc oxide, for example.

The device of the present invention comprises a semiconductor layer (4). This layer may be constituted by a single layer or by several layers, generally has an overall thickness of up to 100 μm, for example up to 60 μm. However, according to an embodiment of the present invention, the semiconductor layer 4 comprises a semiconductor material, wherein said semiconductor layer has a thickness of smaller than 20 μm. The semiconductor layer 4 with a thickness of smaller than 20 microns may also consist of a single layer or comprise two or more separate layers, for example sub-layers. For example, the sub-layers are arranged one above the other, each sub-layer being in continuous contact with the respective one or two neighboring sub-layers. For example, the semiconductor layer may comprise a base semiconductor layer having a comparatively low porosity and thereon a comparatively high porosity semiconductor layer, wherein the sensitizers will preferably or to a larger extent be absorbed on the semiconductor material in the high porosity sub-layer. In other words, the different layers may have different porosity, for example they may be prepared from nanoparticles of different size, but preferably the sizes remain in the ranges given further below. The thickness of the entire semiconductor layer, including all potential sub-layers, is preferably <20 μm, more preferably ≤17 μm, even more preferably ≤15 and most preferably ≤13 μm.

The semiconductor material layer 4 may comprise a semiconductor material selected from Si, TiO$_2$, SnO$_2$, ZnO, WO$_3$, Nb$_2$O$_5$, and TiSrO$_3$, which all are exemplary semiconductor materials for the purpose of the invention. Preferably, the semiconductor material layer 4 comprises a porous layer made of semiconductor nanoparticles, for example nanoparticles made of the semiconductor materials above. The average diameter of the semiconductor nanoparticles preferably lies in the range of 0.5 nm-2000 nm, preferably 1-1000 nm, more preferably 2-500 nm, most preferably 5-100 nm.

The dye is provided in the form of a dye layer 5, which comprises dye molecules according to the present invention, in particular, dyes comprising a compound as defined by formula (I), and/or dyes as defined by formula (89) to (102). The dye molecules are preferably anchored by way of their anchoring group on the surface of the porous nanoparticle layer of the semiconductor layer (4) and form a monomolecular layer thereon.

The charge transport layer 6 preferably comprises (a) an electrically conductive hole and/or electron transporting material or (b) an electrolyte. If the charges are transported by said electrically conductive hole and/or electron transporting material, electrons and/or holes move by electronic motion, instead of diffusion of charged molecules. Such electrically conductive layers are preferably based on organic compounds, including polymers. Accordingly, layer 6 may be an electron and/or hole conducting material such as the amorphous organic hole transport material 2,2',7,7'-tetrakis(N,N-di-p-methoxyphenyl-amine)9,9'-spirofluorene (OMeTAD). In WO2007/107961, charge-transporting materials, which are liquid at room temperature and their application in dye-sensitized solar cells, are disclosed. These materials may be used, for example, for the purpose of the present invention.

If the charge transport layer is an electrolyte, which is preferred, it comprises a redox-couple. Preferred examples of redox couples suitable for dye sensitized solar cells are the I$^-$/I$_3^-$ couple or the Co$^{2+}$/Co$^{3+}$ redox couple (Cobalt tris-polypyridayl complex).

In a further embodiment, the electrolyte comprises one or more ionic liquids, composed ionic liquids or eutectic melt. Ionic liquids are generally defined by the fact that they have a melting point of 100° C. or lower. For example, anions of suitable ionic liquids may be selected from I$^-$, Br$^-$, Cl$^-$, [N(CN)$_2$]$^-$, [N(SO$_2$CF$_3$)$_2$]$^-$, [PF$_6$]$^-$, [BF$_4$]$^-$, [NO$_3$]$^-$, [C(CN)$_3$]$^-$, [B(CN)$_4$]$^-$, [CF$_3$COO]$^-$, [ClO$_4$]$^-$, [BF$_3$CF$_3$]$^-$, [CF$_3$SO$_3$], [CF$_3$F$_2$SO$_3$]$^-$, [CH$_3$H$_2$SO$_3$]$^-$, [(CF$_3$SO$_2$)$_2$N]$^-$, [(C$_2$H$_5$SO$_2$)$_2$N]$^-$, [(CF$_3$SO$_2$)$_3$C]$^-$, [(C$_2$F$_5$SO$_2$)$_3$C]$^-$, [(FSO$_2$)$_3$C]$^-$, [CH$_3$CH$_2$OSO$_3$]$^-$, [CF$_3$C(O)O]$^-$, [CF$_3$CF$_2$C(O)O]$^-$, [CH$_3$CH$_2$C(O)O]$^-$, [CH$_3$C(O)O]$^-$, [P(C$_2$H$_5$)$_3$F$_3$]$^-$, [P(CF$_3$)$_3$F$_3$]$^-$, [P(C$_2$H$_4$H)(CF$_3$)$_2$F$_3$]]$^-$, [P(C$_2$F$_3$H$_2$)$_3$F$_3$]$^-$, [P(C$_2$F$_5$)(CF$_3$)$_2$F$_3$]$^-$, [P(CF$_3$)$_3$F$_3$]$^-$, [P(C$_6$H$_5$)$_3$F$_3$]$^-$, [P(C$_3$H$_7$)$_3$F$_3$]$^-$, [P(C$_4$H$_9$)$_3$F$_3$]$^-$, [P$_2$H$_5$)$_2$F$_3$]$^-$, [(C$_2$H$_5$)$_2$P(O)O]$^-$, [(C$_2$H$_5$)$_2$P(O)O$_2$]$^{2-}$, [PC$_6$H$_5$]$_2$F$_4$]$^-$, [(CF$_3$)$_2$P(O)O]$^-$, [(CH$_3$)$_2$P(O)O]$^-$, [(C$_4$H$_9$)$_2$P(O)O]$^-$, [CF$_3$P(O)O$_2$]$^{2-}$, [CH$_3$P(O)O$_2$]$^{2-}$, [(CH$_3$O)$_2$P(O)O]$^-$, [BF$_2$(C$_2$F$_5$)$_2$]$^-$, [BF$_3$(C$_2$F$_5$)]$^-$, [BF$_2$(CF$_3$)$_2$]$^-$, [B(C$_2$F$_5$)$_4$]$^-$, [BF$_3$(CN)]$^-$, [BF$_2$(CN)$_2$]$^-$, [B(CF$_3$)$_4$]$^-$, [B(OCH$_3$)$_4$]$^-$, [B(OCH$_3$)$_2$(C$_2$H$_5$)]$^-$, [B(O$_2$C$_2$H$_4$)$_2$]$^-$, [B(O$_2$C$_2$H$_2$)$_2$]$^-$, [B(O$_2$CH$_4$)$_2$]$^-$, [N(CF$_3$)$_2$]$^-$, [AlCl$_4$]$^-$ and [SiF$_6$]$^{2-}$.

Cations of ionic liquids according to the invention may, for example, be selected from compounds having structures as shown below:

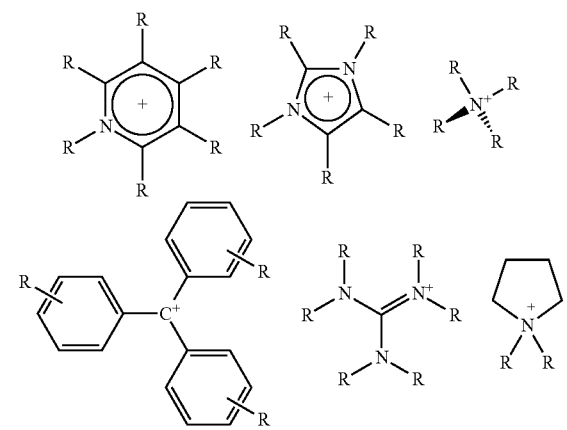

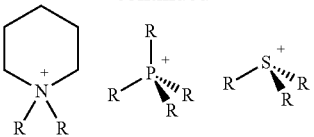

H, provided that at least one R linked to a heteroatom is different from H;

a linear or branched C1-C20 alkyl;

a linear or branched C2-C20 alkenyl, comprising one or several double bonds;

a linear or branched C2-C20 alkynyl, comprising one or several triple bonds;

a saturated, partially or totally unsaturated C3-C7 cycloalkyl;

a halogen, preferably fluoride or chloride, provided that there is no halogen-heteroatom bond;

$NO_2$, provided that there is no bond of this group with a positively charged heteroatom, and that at least one R is different from $NO_2$;

CN, provided that there is no bond of this group with a positively charged heteroatom and that at least one R is different from CN;

wherein the R may be the same or different;

wherein pairs of R may be connected by single or double bonds;

wherein one or several R may be partially or totally substituted with halogens, preferably —F and/or —Cl, or partially with —CN or —$NO_2$, provided that not all R are totally halogenated;

and wherein one or two carbon atoms of any R may or may not be replaced by any heteroatom and/or group selected from the group of —O—, —C(O)—, —C(O)O—, —S—, —S(O)—, $SO_2$—, —$S(O)_2O$—, —P=, —NR'—, —PR'—, —P(O)(OR')—, —P(O)(OR')O—, —P(O)(NR'R')—, —P(O)(NR'R')O—, P(O)(NR'R')NR'—, —S(O)NR'—, and —$S(O)_2NR'$, with R' being H, a C1-C6 alkyl, optionally partially or totally perfluorinated, and/or a phenyl, optionally partially or totally perfluorinated.

wherein any R is independently selected from H and C1-C15 alkyl.

Preferred substituents of the organic cations shown above are disclosed in WO2007/093961, on pages 5-7. The preferred cations defined on these pages are entirely incorporated herein by reference. The most preferred substituents R are independently selected from H and C1-C15 alkyl. Substituents are selected so that indicated positive charge is obtained.

Preferred composed ionic liquids or eutectic melts and electrolytes comprising such composed ionic liquids are disclosed in WO2009/083901 in pages 7-15 and are entirely incorporated herein by reference.

Any alkyl, alkenyl or alkynyl referred to in this specification may be linear, branched or cyclic. Linear alkyls, alkenyls and alkynyls are preferred.

The electrolyte of the device of the invention may comprise two or more ionic liquids Preferably, the electrolyte is substantially free of a solvent. Substantially free of a solvent means that there is less than 25 vol. % of added solvent of high boiling point (more than 200° C.), preferably no added solvent. More preferably, substantially free of a solvent means that there is less than 5 vol. % of added solvent.

The counter electrode 7 may comprise or consist of Pt, Au, Ni, Cu, Ag, In, Ru, Pd, Rh, Ir, Os, C, CoS, conductive polymer or a combination comprising two or more of the aforementioned. Examples of conductive polymers from which a suitable counter electrode material may be selected are polymers comprising polyaniline, polypyrrole, polythiophene, polybenzene and acetylene.

The present invention will now be illustrated by way of examples. These examples do not limit the scope of this invention, which is defined by the appended claims.

EXAMPLES

Example 1

Synthesis of Compound of Formula (89) or Dye Y789

The general scheme of the synthesis of compound of formula (89) or dye Y789 is shown in FIG. 1.

Synthesis of [5-Bromo-15-Bis(2',4'-dihexoxybiphenyl-4-yl)amino-10,20-bis(2,6-didodecoxyphenyl)-porphyrinato] Zinc(II) (Compound 2 in Scheme of FIG. 1)

In an inert atmosphere, 140 mg (0.1 mM) of [5,15-Dibromo-10,20-bis(2,6-didodecoxyphenyl)porphyrinato] zinc(II) was reacted with 110 mg (0.15 mM) of bis(2',4'-dihexoxybiphenyl-4-yl)amine catalyzed with 5 mg (0.01 mM) $Pd(Pt-Bu_3)_2$ in the presence of 50 mg (0.5 mM) t-BuONa in 5 mL toluene at 110° C. for 12 h, then the mixture was cooled to room temperature and poured to 50 mL water. After that the mixture was extracted twice with 50 mL $CH_2Cl_2$, the organic phase was combined and evaporated. The residue was subject to silica gel column chromatography using a mixture of 1:1 $CH_2Cl_2$ and hexane as eluent, yielded 150 mg (75%) purple waxy product. $^1$H NMR (400 MHz, Chloroform-d) δ 9.68 (d, J=4.6 Hz, 2H), 9.29 (d, J=4.6 Hz, 2H), 8.88 (d, J=4.6 Hz, 2H), 8.74 (d, J=4.6 Hz, 2H), 7.66 (t, J=8.4 Hz, 2H), 7.37 (d, J=1.7 Hz, 8H), 7.16 (d, J=8.5 Hz, 2H), 6.97 (d, J=8.5 Hz, 4H), 6.54-6.40 (m, 4H), 4.01-3.75 (m, 16H), 1.84-1.62 (m, 16H), 1.61-0.37 (m, 120H).

Synthesis of [5-ethynyl-15-Bis(2',4'-dihexoxybiphenyl-4-yl)amino-10,20-bis(2,6-didodecoxyphenyl)-porphyrinato] Zinc(II) (Compound 3 in Scheme of FIG. 1)

A mixture of [5-Bromo-15-Bis(2',4'-dihexoxybiphenyl-4-yl)amino-10,20-bis(2,6-didodecoxyphenyl)-porphyrinato] Zinc(II) 200 mg (0.1 mM) and 50 mg (0.5 mM) trimethylsilylacetylene, 9 mg (0.01 mM) $Pd_2(dba)_3$ and 5.2 mg (0.02 mM) triphenylphosphine in 2 mL triethylamine was heated to 60° C. for 4 h, then the mixture was cooled to room temperature and the solvent was evaporated. The residue was purified by silica gel column chromatography, washed with 1:1 $CH_2Cl_2$ and hexane to get green oil. Then the oil was reacted with 60 mg (0.2 mM) $Bu_4NF$ in THF at room temperature for 1 h to remove the trimethylsilyl protecting group. The solvent was removed by vacuum and the residue was purified by silica gel column with 1:1 $CH_2Cl_2$ and hexane as eluent, yielded 120 mg (60%) product. $^1$H NMR (400 MHz, Chloroform-d) δ 9.65 (d, J=4.6 Hz, 2H), 9.31 (d, J=4.6 Hz, 2H), 8.91 (d, J=4.6 Hz, 2H), 8.76 (d, J=4.6 Hz, 2H), 7.69 (t, J=8.4 Hz, 2H), 7.37 (s, 8H), 7.17 (d, J=8.5 Hz, 2H), 6.99 (d, J=8.5 Hz, 4H), 6.58-6.40 (m, 4H), 4.10 (s, 1H), 4.01-3.79 (m, 16H), 1.90-1.64 (m, 16H), 1.57-0.44 (m, 120H).

Synthesis of Compound 4 in Scheme of FIG. 1

To a mixture of [5-ethynyl-15-Bis(2',4'-dihexoxybiphenyl-4-yl)amino-10,20-bis(2,6-didodecoxyphenyl)-porphyrinato] Zinc(II) 200 mg (0.1 mM) and methyl 4-(8-bromo-2,3-diphenylquinoxalin-5-yl)benzoate 50 mg (0.1 mM) in 5 mL triethylamine, $Pd_2(dba)_3$ and 5.2 mg (0.02 mM) triphenylphosphine was added. The mixture was heated at 60° C. for 24 h under the protection of $N_2$ gas. After evaporating the solvent, the residue was purified by silica gel column eluented with a mixture of 2:1 $CH_2Cl_2$ and hexane to yield 110 mg (50%) dark green solid product. $^1H$ NMR (400 MHz, Chloroform-d) δ 10.16 (d, J=4.6 Hz, 2H), 9.28 (d, J=4.6 Hz, 2H), 8.82 (d, J=4.6 Hz, 2H), 8.76 (d, J=4.6 Hz, 2H), 8.51 (d, J=7.6 Hz, 1H), 8.25 (d, J=8.3 Hz, 2H), 8.09-8.00 (m, 6H), 7.76-7.65 (m, 5H), 7.49 (dd, J=5.1, 2.0 Hz, 2H), 7.44-7.33 (m, 10H), 7.17 (d, J=8.5 Hz, 2H), 7.02 (d, J=8.5 Hz, 4H), 6.54-6.41 (m, 4H), 4.00 (s, 3H), 3.98-3.83 (m, 16H), 1.94-1.55 (m, 24H), 1.50-0.39 (m, 112H).

Synthesis of Dye Y789 (Compound of Formula (89))

5 mL ethanol and 1 mL water was added to a mixture of 48 mg (0.02 mM) and LiOH 26 mg (1 mM), the mixture was stirred at room temperature for 4 h. The mixture was poured into 50 mL water, and extracted with 50 mL $CH_2Cl_2$ twice, the organic phase was combined and evaporated. After purifying with silica gel column, 36 mg dark green solid was produced. $^1H$ NMR (400 MHz, Chloroform-d) δ 10.12 (d, J=4.5 Hz, 2H), 9.24 (d, J=4.5 Hz, 2H), 8.78 (d, J=4.5 Hz, 2H), 8.71 (d, J=4.6 Hz, 2H), 8.49 (d, J=7.6 Hz, 1H), 8.28 (d, J=8.0 Hz, 2H), 8.12-7.98 (m, 6H), 7.77-7.63 (m, 5H), 7.47 (dd, J=4.8, 2.3 Hz, 2H), 7.43-7.31 (m, 10H), 7.15 (d, J=8.5 Hz, 2H), 7.01 (d, J=8.4 Hz, 4H), 6.55-6.41 (m, 4H), 4.11-3.75 (m, 16H), 1.95-1.55 (m, 24H), 1.55-1.20 (m, 32H), 1.20-0.39 (m, 80H). APCI: m/z calcd for $C_{159}H_{197}N_7O_{10}Zn$ 2405.4447, found 2405.4405.

Example 2

Figure 2:
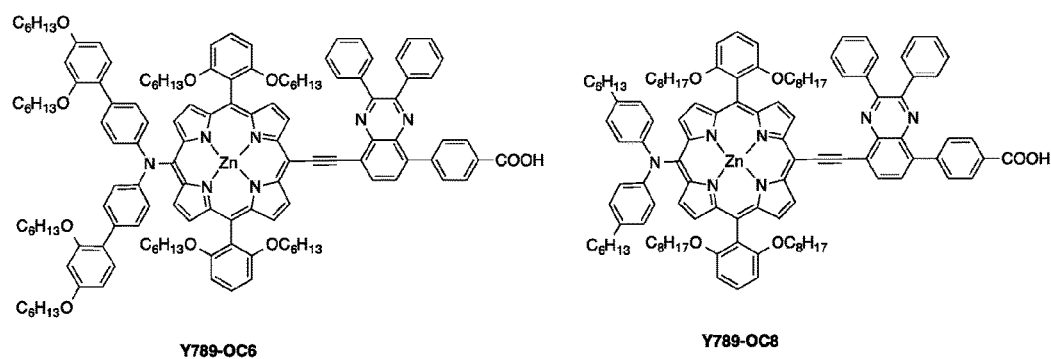
FIG. 2 shows dyes Y789-OC6 and Y789-OC8.

Synthesis of Compounds Y789-OC6 and Y789-OC8 (FIG. 2)

The Y789-OC6 and Y789-OC8 was synthesized following the synthetic procedure of the Y789, namely compound of formula (89). Both compounds are illustrated in FIG. 2.

The characterization data for Y789-OC6 is as following: $^1H$ NMR (400 MHz, Chloroform-d) δ 10.13 (d, J=4.4 Hz, 2H), 9.26 (d, J=4.5 Hz, 2H), 8.80 (d, J=4.5 Hz, 2H), 8.73 (d, J=4.5 Hz, 2H), 8.51 (d, J=7.5 Hz, 1H), 8.30 (d, J=8.2 Hz, 2H), 8.13-8.07 (m, 2H), 8.07-7.99 (m, 4H), 7.74-7.65 (m, 5H), 7.47 (dd, J=5.2, 2.0 Hz, 2H), 7.39-7.33 (m, 10H), 7.16 (d, J=8.5 Hz, 2H), 7.05-6.96 (m, 4H), 6.52-6.41 (m, 4H), 3.97-3.83 (m, 16H), 1.86-1.62 (m, 12H), 1.59-0.12 (m, 76H). APCI: m/z calcd for $C_{133}H_{149}N_7O_{10}Zn$ 2068.0657, found 2068.0651.

The characterization data for Y789-OC8 is as following: $^1H$ NMR (400 MHz, Chloroform-d) δ 10.12 (d, J=4.5 Hz, 2H), 9.18 (d, J=4.5 Hz, 2H), 8.79 (d, J=4.6 Hz, 2H), 8.70 (d, J=4.6 Hz, 2H), 8.50 (d, J=7.6 Hz, 1H), 8.28 (d, J=8.1 Hz, 2H), 8.12-7.99 (m, 5H), 7.75-7.65 (m, 4H), 7.47 (dd, J=5.1, 2.0 Hz, 4H), 7.38 (dd, J=5.6, 3.7 Hz, 2H), 7.25-7.20 (m, 4H), 7.01 (d, J=8.4 Hz, 4H), 6.94 (d, J=8.7 Hz, 4H), 3.86 (t, J=6.6 Hz, 8H), 2.47 (t, J=7.8 Hz, 4H), 1.62-0.33 (m, 82H). APCI: m/z calcd for $C_{117}H_{133}N_7O_6Zn$ 1795.9609, found 1795.9615.

Example 3

Photovoltaic Characteristics of Dye Y789 and Dye Y350

Figure 3:
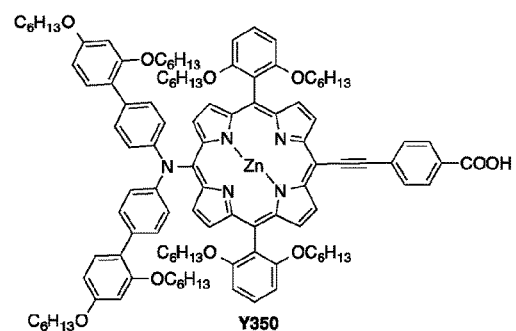
FIG. 3 shows dye Y350.

In the dye Y789, quinaxoline moiety is used as the π-conjugated linker between the porphyrin core and anchoring group being benzoic acid. Said π-conjugated linker, quinaxoline based acceptor, is absent from the dye Y350, of which the structure is shown in FIG. 3.

Figure 4:
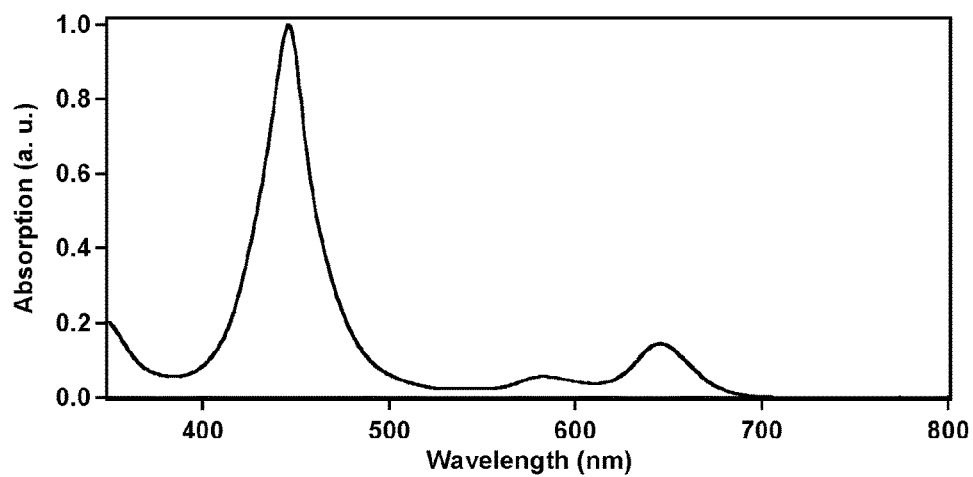
FIG. 4 shows the absorption spectra as a function of wavelength of dye Y350 (FIG. 4A) and of dye Y789 (compound of formula (89)—FIG. 4B).
Figure 4:
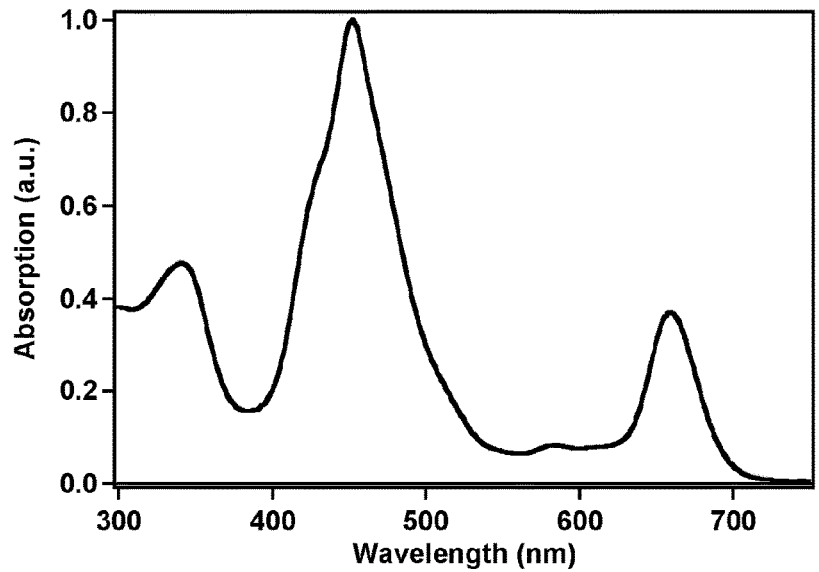

Both porphyrin based dyes exhibit absorption maxima in the 400-500 nm and 600-700 nm, with a further absorption maximum in 300-400 nm for the dye Y789 (see FIGS. 4A and 4B). The absorption in 600-700 nm of dye Y789 is quite doubled compared with the absorption of Y350 at these wavelengths. This effect is attributed to the effect of the insertion of the electron-withdrawing quinaxoline based acceptor as a π-conjugated linker between the porphyrin and the anchoring group.

Figure 5:
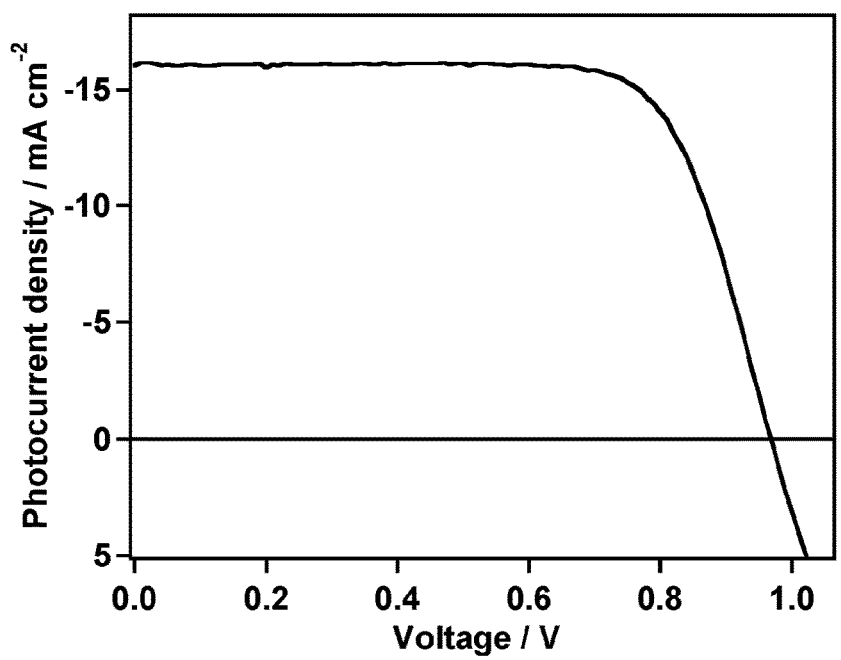
FIG. 5 shows the J-V (photocurrent density-voltage) curves of dye Y350 (FIG. 5A) and of dye Y789 (compound of formula (89)—FIG. 5B) under simulated one sun illumination (AM1.5 G, 100 mW/cm²).
Figure 5:
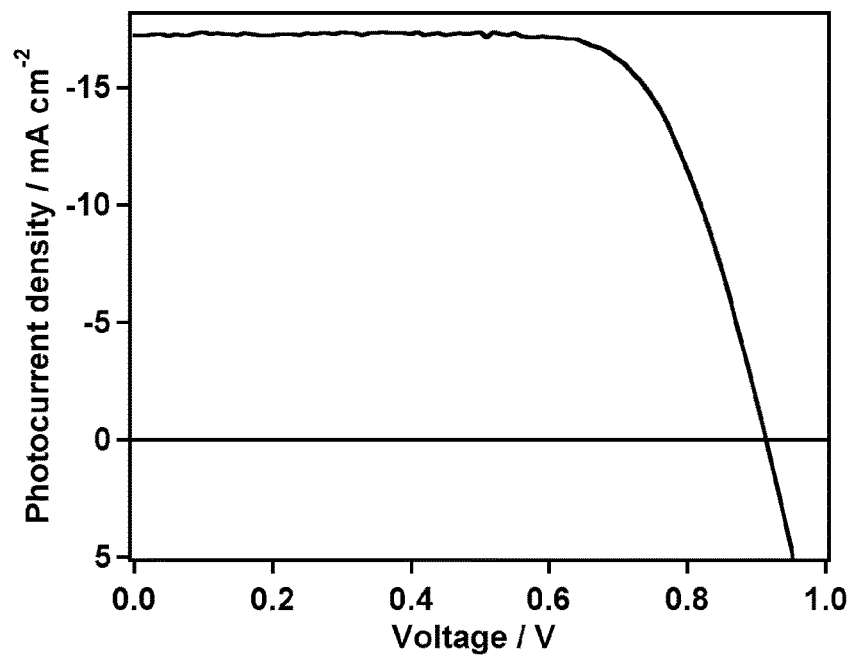
Figure 6:
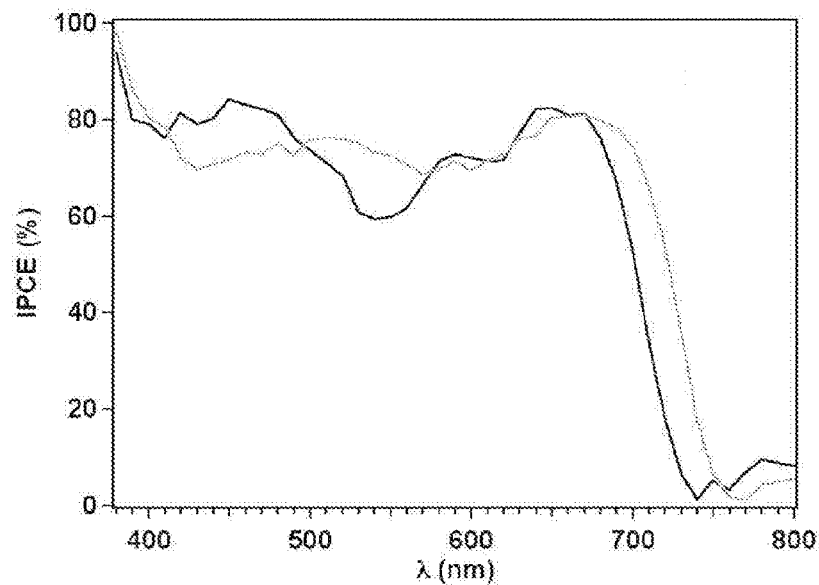
FIG. 6 shows IPCE (incident photon-to-electric current conversion) spectra as a function of wavelength of dye Y350 (dark line) and of dye Y789 (light line) sensitized DSCs.

The photovoltaic performance of the two dyes Y789, Y350 was evaluated by using them in the DSCs using cobalt tris-bipyridine based redox mediator in acetonitrile. The composition of the cobalt electrolyte is as follows: 0.1 M lithium trifluoromethanesulfonimide (LiTFSI), 0.055 M [Co(bpy)$_3$](TFSI)$_3$, 0.2 M [Co(bpy)$_3$](TFSI)$_2$, 0.8 M tert-butyl pyridine (TBP) in acetonitrile. The current-voltage (J-V) characteristics of these devices under simulated one sun illumination (AM1.5 G, 100 mW/cm$^2$) are presented in FIGS. 5A and 5B and FIG. 6, and the corresponding photovoltaic data is summarized in Table 1.

TABLE 1

Detailed photovoltaic parameters obtained with Y350 and Y789 dyes using cobalt tris-bipyridine redox electrolyte

| Dye | Redox | Power$_{in}$ [mW/cm$^2$] | $J_{SC}$ [mW/cm$^2$] | $V_{OC}$ [mV] | FF | PCE [%] |
|---|---|---|---|---|---|---|
| Y350 | Co$^{2+}$/Co$^{3+}$ | 9.3 | 1.67 | 707 | 0.78 | 11.8 |
|  |  | 50.6 | 8.92 | 722 | 0.71 | 11.5 |
|  |  | 99 | 16.19 | 715 | 0.69 | 10.6 |
| Y789 | Co$^{2+}$/Co$^{3+}$ | 9.6 | 1.92 | 712 | 0.76 | 13.2 |
|  |  | 49.9 | 9.83 | 732 | 0.75 | 13.5 |
|  |  | 96.7 | 17.38 | 712 | 0.72 | 12.0 |

By introducing an electro-withdrawing quinoxaline acceptor between the porphyrin core and anchoring benzoic acid, porphyrin dye Y789 shows a broad absorption covering the whole Visible to near-IR spectral range. Compared with the reference porphyrin sensitizer Y350 without the quinoxaline acceptor, the new porphyrin dye Y789 bridges the absorption gap between the Soret band and Q band and shows a red-shifted spectrum (see FIGS. 4A and B and FIG. 6).

In the study in DSCs using the state-of-art Co$^{+2/+3}$(bipyridine)$_3$ complex-based electrolyte, high open-circuit voltage and high energy conversion efficiency of 13.5% at Power$_{in}$ corresponding up to half sunlight was reached. This is the highest power conversion efficiency obtained with a single dye sensitized DSC device.

Previously, co-sensitization with organic dyes showing complementary absorption spectra, was used to fill the gap between the Soret band and Q-band. In the case of Y789 dye, it is evident from the IPCE spectrum that the broadening of the Soret band resulted in the filling of the gap between the Soret band and the Q-bands typically which is not observed in case of all the porphyrins utilized in the DSCs earlier Therefore the introduction of electron-withdrawing group between the porphyrin core and anchoring group opens a new way to further shift the absorption spectra to further red and improve the energy conversion efficiency of the porphyrin dye-sensitized solar cells.

The invention claimed is:
1. A compound of formula (I)

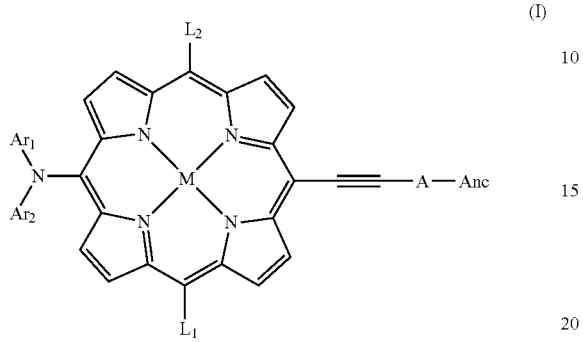

(I)

wherein
M is selected from Co, Cu, Fe, Mg, Mn, Ni, Si or Zn or M is two H (hydrogen) substituting two pyrrole moieties constituting the porphyrin core;
A is an acceptor group selected from a moiety according to any one of the formulae (1) to (36) and (103) to (105)

(1)

(2)

(3)

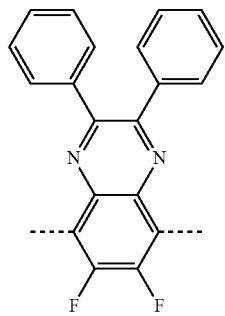

(4)

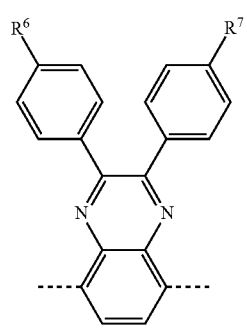

(5)

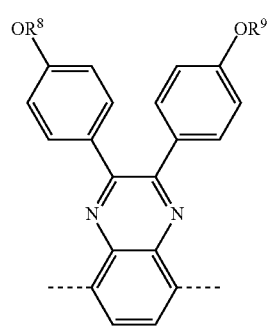

(6)

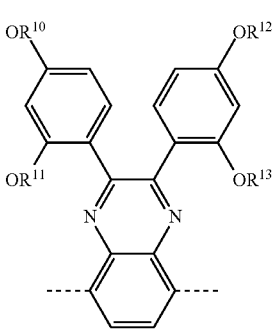

(7)

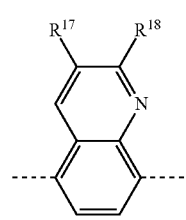

(8)

(9) 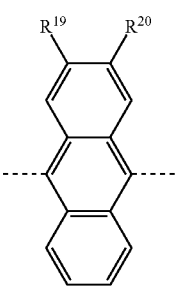
(10) 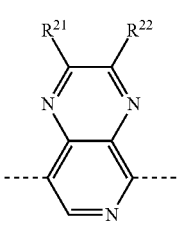
(11) 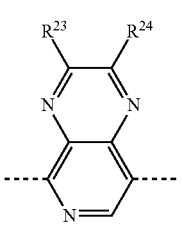
(12) 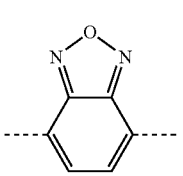
(13) 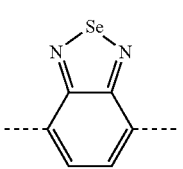
(14) 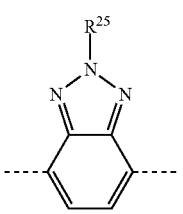
(15) 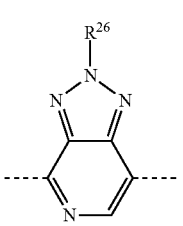
(16) 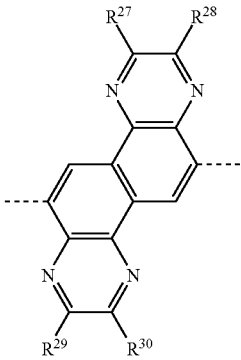
(17) 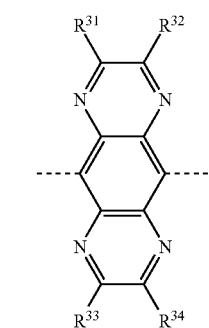
(18) 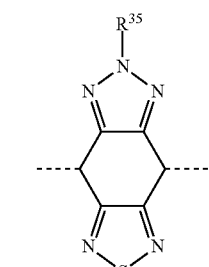
(19) 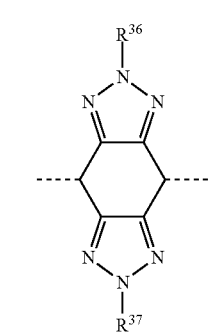
(20) 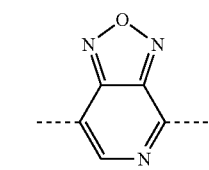
(21) 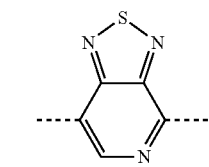

-continued
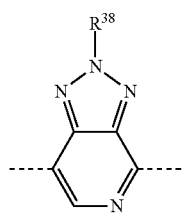
(22)
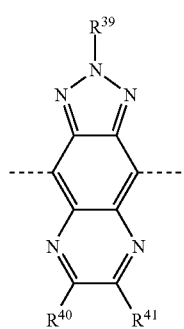
(23)
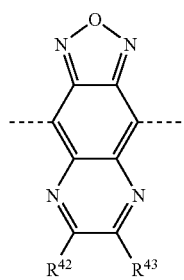
(24)
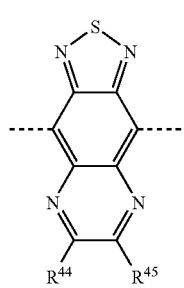
(25)
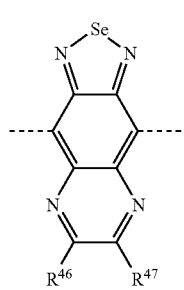
(26)
-continued
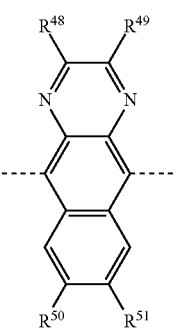
(27)
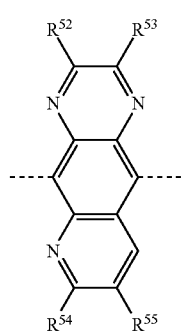
(28)
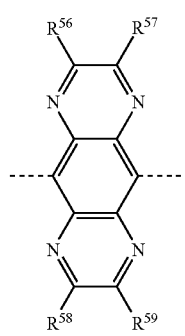
(29)
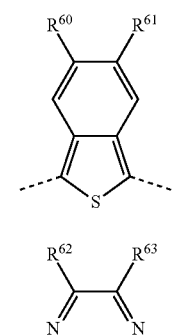
(30)
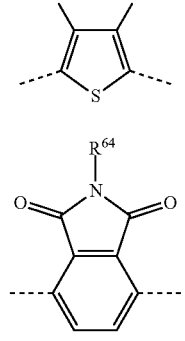
(31)
(32)

(33) 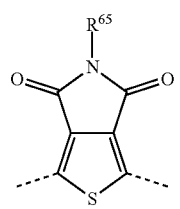
(34) 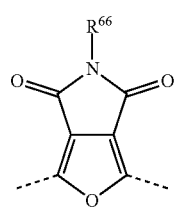
(35) 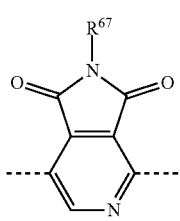
(36) 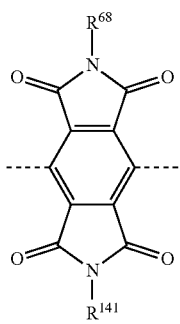
(103) 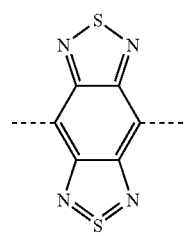
(104) 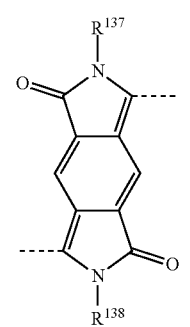
(105) 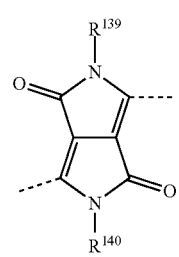
wherein $R^1$-$R^2$, $R^4$-$R^{13}$, $R^{17}$-$R^{68}$ and $R^{137}$-$R^{141}$ are substituents independently selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N;
Anc is an anchoring group selected from a moiety according to any one of formulae (37) to (53)
(37) 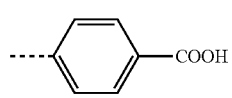
(38) 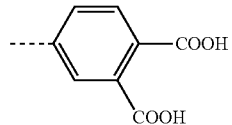
(39) 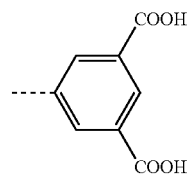
(40) 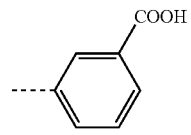
(41) 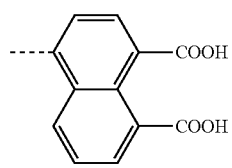
(42) 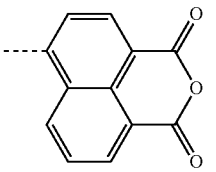
(43) 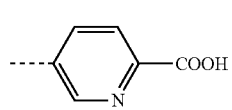

-continued
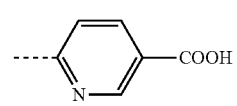 (44)
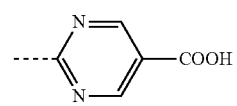 (45)
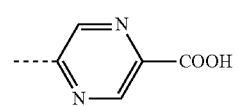 (46)
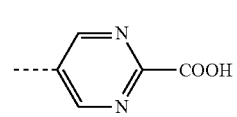 (47)
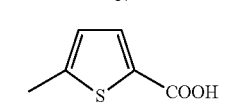 (48)
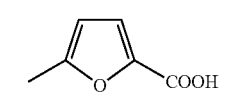 (49)
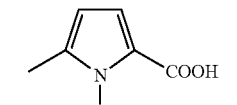 (50)
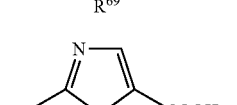 (51)
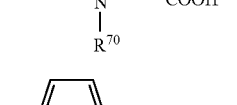 (52)
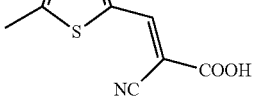 (53)
wherein $R^{69}$ and $R^{70}$ are substituents independently selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N;
$L_1$ and $L_2$ are substituents independently selected from a moiety according to any one of formulae (54) to (65)
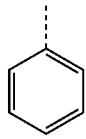 (54)
-continued
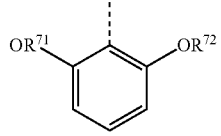 (55)
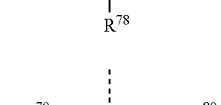 (56)
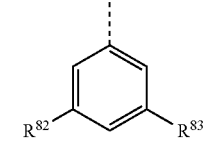 (57)
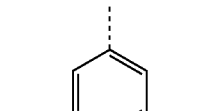 (58)
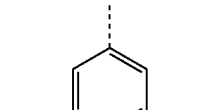 (59)
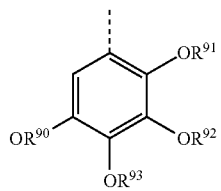 (60)
(61)
(62)

(63)
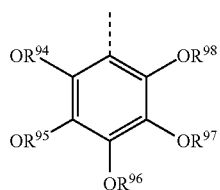
(64)
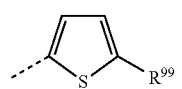
(65)
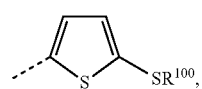
wherein $R^{71}$-$R^{100}$ are substituents independently selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N;
$Ar_1$ and $Ar_2$ are donor substituents being selected from a moiety according to any one of formulae (66) to (88)
(66)
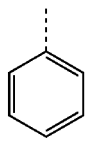
(67)
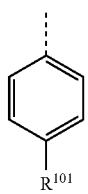
(68)
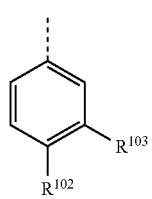
(69)
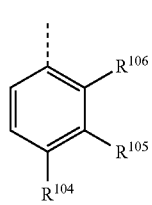
(70)
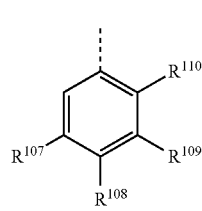
(71)
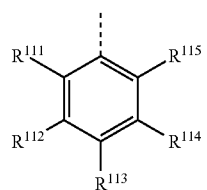
(72)
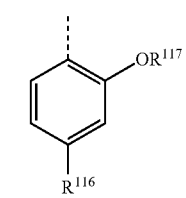
(73)
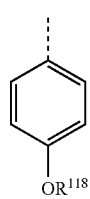
(74)
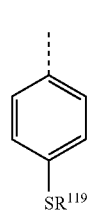
(75)
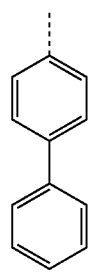
(76)
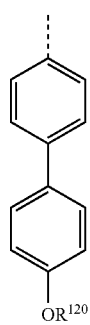

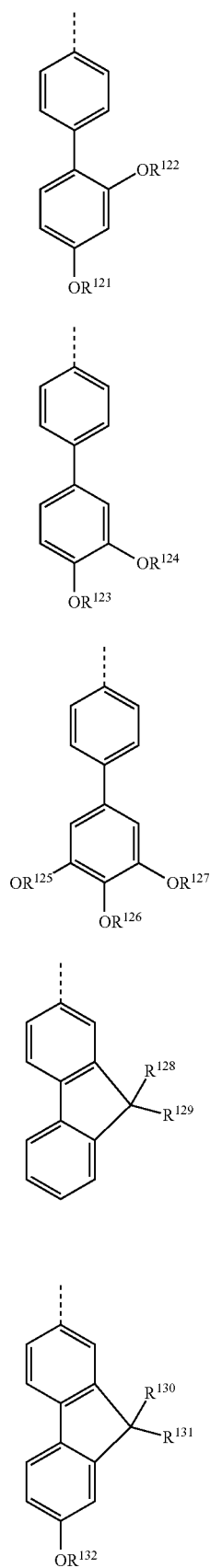

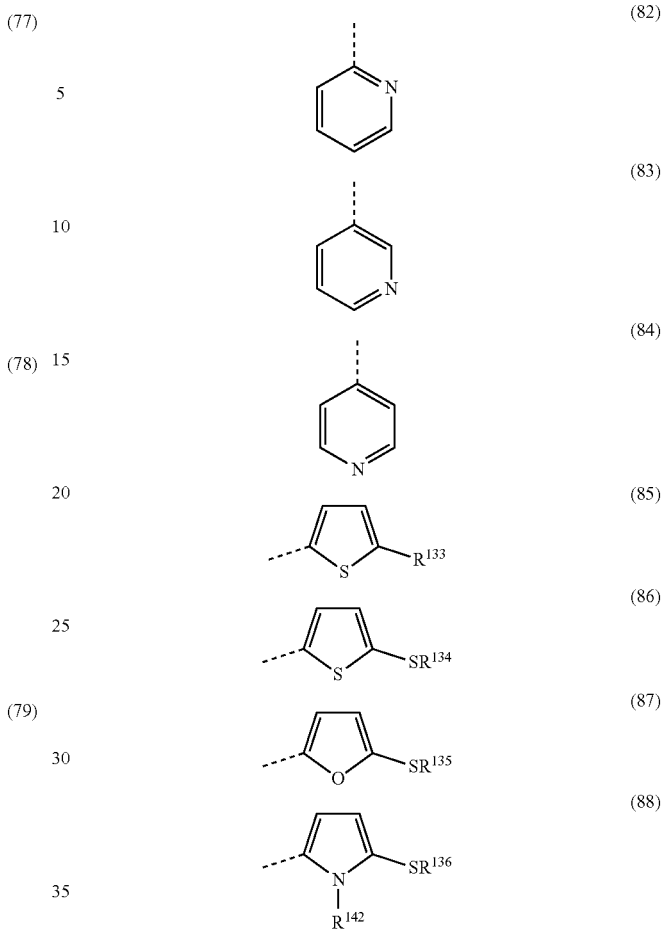

wherein $R^{101}$-$R^{136}$ and $R^{142}$ are substituents independently selected from H, C1-C16 alkyl, C1-C16 alkoxy, C1-C16 thioalkyl, C1-C16 alkoxyalkyl, C4-C16 aryl, C1-C16 arylalkyl or C4-C16 heteroaryl, C4-C16 heteroarylalkyl wherein heteroatoms are selected from O, S, or N.

2. The compound of formula (I) according to claim 1, wherein A is selected from a moiety according to any one of the formulae (1)-(12), (14), (15), (25), (27), (30), and (31).

3. The compound of formula (I) according to claim 1, wherein Anc is selected from a moiety according to any one of the formulae (37) to (47).

4. The compound of formula (I) according to claim 1, wherein $Ar_1$ and $Ar_2$ are selected from a moiety according to any one of the formulae (67), (75) to (81).

5. The compound of formula (I) according to claim 1, wherein $L_1$ and $L_2$ are selected from a moiety according to any one of the formulae (55) to (58).

6. The compound of formula (I) according to claim 1, wherein $Ar_1$ and $Ar_2$ are identical moieties.

7. The compound of formula (I) according to claim 1, wherein $L_1$ and $L_2$ are identical moieties.

8. The compound of formula (I) according to claim 1, wherein $Ar_1$ and $Ar_2$ are moiety (77).

9. The compound of formula (I) according to claim 1, wherein $L_1$ and $L_2$ are moiety (55).

10. A dye or a sensitizing compound of an electrochemical or optoelectronic device comprising a compound of formula (I) according to claim 1.

11. An electrochemical or optoelectronic device comprising a dye being a compound of formula (I) according to claim 1.

12. The device according to claim 11, wherein said device is selected from an electrochemical device, a photo-electrochemical device, an optoelectronic device, a light emitting device, an electrochromic or photo-electrochromic device, an electrochemical sensor, an electrochemical display or a dye sensitized solar cell.

* * * * *

UNITED STATES PATENT AND TRADEMARK OFFICE
CERTIFICATE OF CORRECTION

PATENT NO. : 9,812,658 B2
APPLICATION NO. : 15/101975
DATED : November 7, 2017
INVENTOR(S) : Chenyi Yi et al.

Page 1 of 1

It is certified that error appears in the above-identified patent and that said Letters Patent is hereby corrected as shown below:

In the Specification

Column 46
- Line 37: "...[P$_2$H$_5$)$_2$F$_3$]$^-$, ..." to be replaced with "...[P(C$_2$H$_5$)$_2$F$_4$]$^-$, ..."

Column 47
- Line 36: "...-S(O)$_2$O-, -P=, ..." to be replaced with "...-S(O)$_2$O-, -N=, -P=, ..."

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*